US007649097B2

(12) United States Patent
Jasti et al.

(10) Patent No.: US 7,649,097 B2
(45) Date of Patent: Jan. 19, 2010

(54) TETRACYCLIC ARYLSULFONYL INDOLES HAVING SEROTONIN RECEPTOR AFFINITY USEFUL AS THERAPEUTIC AGENTS, PROCESS FOR THEIR PREPARATION AND PHARMACEUTICAL COMPOSITIONS CONTAINING THEM

(75) Inventors: Venkateswarlu Jasti, Hyderabad (IN); Venkata Satya Nirogi Ramakrishna, Hyderabad (IN); Rama Sastri Kambhampati, Hyderabad (IN); Srinivasa Reddy Battula, Hyderabad (IN); Arava Veeraraeddy, Hyderabad (IN); Venkata Satya Veerabhadra Vadlamudi Rao, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 587 days.

(21) Appl. No.: 10/519,219

(22) PCT Filed: Jun. 19, 2003

(86) PCT No.: PCT/IN03/00222

§ 371 (c)(1),
(2), (4) Date: May 13, 2005

(87) PCT Pub. No.: WO04/000849

PCT Pub. Date: Dec. 31, 2003

(65) Prior Publication Data

US 2005/0203154 A1 Sep. 15, 2005

(30) Foreign Application Priority Data

Jun. 21, 2002 (IN) .......................... 478/MAS/2002

(51) Int. Cl.
*A61K 31/425* (2006.01)
*C07D 513/04* (2006.01)
(52) U.S. Cl. .................. 548/207; 514/373; 548/209
(58) Field of Classification Search ............ 548/209, 548/207
See application file for complete search history.

(56) References Cited

U.S. PATENT DOCUMENTS

| 3,481,953 A | * | 12/1969 | Herbst .......................... 548/468 |
| 4,839,377 A | | 6/1989 | Bays et al. |
| 4,855,314 A | | 8/1989 | Oxford et al. |

FOREIGN PATENT DOCUMENTS

| EP | 0 303 506 | 2/1989 |
| EP | 0 354 777 | 2/1990 |
| EP | 0 438 230 | 7/1991 |
| EP | 0 497 512 | 8/1992 |
| EP | 0 313 397 | 6/1993 |
| EP | 0 457 701 | 2/1995 |
| GB | 2 035 310 | 6/1980 |
| GB | 2 341 549 | 3/2000 |
| JP | A 2000-026471 | 1/2000 |
| WO | WO 91/18897 | 12/1991 |
| WO | WO 93/00086 | 1/1993 |
| WO | WO 93/23396 | 11/1993 |
| WO | WO 94/06769 | 3/1994 |
| WO | WO 00/34242 | 6/2000 |
| WO | WO 02/078693 | 10/2002 |

OTHER PUBLICATIONS

Crich, et al., Journal of the Chemical Society Chemical Communications (1989), (19), 1418-1419.*
Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Gaster {Annual Reports in Medicinal Chemistry, vol. 33 (1998), pp. 21-30.*
Isaac, Bioorganic & Medicinal Chemistry Letters, vol. 10 (2000), pp. 919-921.*
Nitsch et al., Journal of Biological Chemistry, vol. 271, (1996), pp. 4188-4194.*
Thomas A. Godwin (Gastrointestinal Diseases, http://edcenter.med.cornell.edu/CUMC_PathNotes/Gastrointestinal/Gastrointestinal.html, Aug. 2004, 51 pages.*
Glennon, Richard A., et al., 2000, 2-Substituted Tryptamines: Agents with Selectivity for 5-$HT_6$ Serotonin Receptors. *J. Med. Chem.* 43:1011-1018.
Tsai, Yuching, et al.,2000; $N_1$-(Benzenesulfonyl)tryptamines as Novel 5-$H5_5$ Antagonists. *Bioorganic & Medicinal Chemistry Letters* 10:2295-2299.
Boess, Frank G., at al.,1998, The 5-Hydoxytryptamine$_6$ Receptor-Selective radioligand [$^3$H]Ro 63-0653 Labels 5-Hydroxytryptamine Receptor Binding Sites in Rat and Porcine Striatum. *Molecular Pharmacology* 54:577-583.
Bourson, Anne, at al.,1998, Involvement of 5-$HT_6$ receptors in nigrostriatal function in rodents. *British Journal of Pharmacology* 125:1562-1566.

(Continued)

*Primary Examiner*—Laura L. Stockton
(74) *Attorney, Agent, or Firm*—Darby & Darby

(57) ABSTRACT

The present invention relates to novel tetracyclic arylsulfonyl indoles, their derivatives, their analogues, their tautomeric forms, their stereoisomers, their polymorphs, their pharmaceutically acceptable salts, their pharmaceutically acceptable solvates, novel intermediates described herein and pharmaceutically acceptable compositions containing them. This invention particularly relates to novel tetracyclic arylsulfonyl indoles of the general formula (I), their derivatives, their analogues, their tautomeric forms, their stereoisomers, their polymorphs, their pharmaceutically acceptable salts, their pharmaceutically acceptable solvates, novel intermediates described herein and pharmaceutically acceptable compositions containing them. This invention also relates to process/es for preparing such compound/s of general formula (I), composition/s containing effective amount/s of such a compound and the use of such a compound/composition in therapy.

7 Claims, No Drawings

OTHER PUBLICATIONS

Sleight, Andrew J. et al.,1998, Characterization of Ro 04-6790 and Ro 63-0563: potent and selective antagonists at human and rat 5-HT$_5$ receptors. *British Journal of Pharmacology* 124:556-562.

Yoshioka, M., at at.,1998, Central Distribution and Function of 5-HT$_6$ Receptor Subtype in the Rat Brain. *Life Sciences* 62(17/18):1473-1477.

Hoyer, Daniel, et al.,1994, VII. International Union of Pharmacology Classification of Receptors for 5-Hydroxytryptamine (Serotonin). *Pharmacological Reviews* 46(2)157-203.

Martin, G.R. And P.P.A. Humphrey.,1994, Receptors for 5-Hydroxytryptamine: Current Perspectives on Classification and Nomenclature. Neuropharmacology 33(3/4)261-273.

Rees, Stephen, et al.,1994, Cloning and Characterisation of the human 5-HT5A serotonin receptor. *FEBS Letters* 355(242-246).

Roth, Bryan L., et al.,1994, Binding of Typical and Atypical Antipsychotic Agents to 5-Hydroxytryptamine-6 and 5-Hydroxytryptamine-7 Receptors. *The Journal of Pharmacology and Experimental Therapeutics* 268(3):1403-1410.

Grossman, C.J., et al., 1993, Development of a radioligand binding assay for 5-HT$_4$ receptors in guina-pig and rat brain. *British Journal of Pharmacology* 109:618-624.

Monsma, Jr., Frederick J., et al., 1993, Cloning and Expression of a Novel Serotonin Receptor with High Affinity for Tricyclic Psychotropic Drugs. *Molecular Pharmacology* 43:320-327.

Ruat, Martial, et al.,1993, A Novel Rat Serotonin (5-HT6) Receptor Molecular Cloning, Localization and Stimulation of Camp Accumulation. *Biochemical and Biophysical Research Communications* 193(1):268-276.

Schoeffter, Philippe, et al.,1993, SDZ 216-525, a selective and potent 5-HT$_{1A}$ receptor antagonist. *European Journal of Pharmacology—Molecular Pharmacology Section* 244:251-257.

Shen, Yong, et al.,1993, Molecular Cloning and Expression of 5-Hydroxytryptamine$_7$ Serotonin Receptor Subtype. *The Journal of Biological Chemistry* 268(24):18200-18204.

Spadoni, Gilberto.,1993, 2-Substituted 5-Methoxy-*N*-acyltryptamines: Synthesis, Binding Affinity for the Melatonin Receptor, and Evaluation of the Biological Activity. *J. Med. Chem.* 36:4069-4074.

Glennon, Richard A., 1990, Serotonin Receptors: Clinical Implications. *Neuroscience & Biobehavioral Reviews* 14:35-47.

Lummis, Sarah C.R., et al., 1990, Characterization of 5-HT3 receptors in intact N1E-115 neuroblastoma cells. *European Journal of Pharmacology—Molecular Pharmacology Section* 189:223-227.

Saxena, Pramod R. and Carlos M. Villalón.,1990, Cardiovascular Effects of Serotonin Agonists and Antagonists. *Journal of Cardiovascular Pharmacology* 15(7):S17-S34.

Gershon, Michael D., et al.,1989, 5-Hydroxytryptamine and enteric neurones. *In* the Peripheral Actions of 5-Hydroxytryptamine. J. Fozard, editor. Oxford University Press, Oxford. 247-273.

Schoeffter, Philippe and Daniel Hoyer.,1989, How selective is GR 43175? Interactions with functional 5-HT$_{1A}$, 5-HT$_{1B}$, 5-HT$_{1C}$ and 5-HT$_{1D}$ receptors. *Naunyn-Schmiedeberg's Arch. Pharmacol.* 340:135-138.

Waeber, C., et al.,1988, Molecular Pharmacology of 5-HT1D recognition sites: Radioligand binding studies in human, pig and calf brain membranes. *Naunyn-Schmiedeberg's Arch. Pharmacol.* 337:595-601.

Hoyer, Daniel and Hans C. Neijt., 1988, Identification of Serotonin 5-HT$_3$ Recognition Sites in Membranes of N1E-115 Neuroblistoma Cells by Radioligand Binding. *Molecular Pharmacology* 33:303-309.

Hoyer, Daniel, et al.,1985, Molecular Pharmacology of 5-HT$_1$ and 5-HT$_2$ Recognition Sites in Rat and Pig Brain Membranes: Radiollgand Binding Studies with [$^3$H]5-HT, [$^3$H]8-OH-DPAT, (-)[$^{125}$I]Iodocyanopindolol, [$^3$H]Mesulergine and [3H]Ketanserin. *European Journal of Pharmacology* 118:13-23.

Pazos, Angel, et al., 1985, The Binding of Serotonergic Ligands to the Porcine Choroid Plexus: Characterization of a New Type of Serotonin Recognition Site. *European Journal of Pharmacology* 106:539-546.

Fuller, R.W.,1982, Drugs Acting on Serotonergic Neuronal Systems, in Biology of Serotonergic Transmission. Neville N. Osborn, ed. John Wiley & Sons. Chichester. 221-247.

Leysen, J.E., et al.,1981 [$^3$H]Ketanserin (R 41 468), a Selective 3H-Ligand for Serotonin$_2$, Receptor Binding Sites.Binding Properties, Brain Distribution, and Functional Role. *Molecular Pharmacology* 21:301-314.

Baldwin, J.E.,ed. 1996, Reduction of Carbon-Carbon Bonds in Principles of Asymmetric Synthesis. 311-316.

Tyers, M.B.,1991, 5-HT$_3$ receptors and the therapeutic potential of 5-HT$_3$ receptor antagonists. *Therapie.* 46:431-436.

Russell M.G. et al., 2001, N-Arylsulfonylindole derivatives as serotonin 5-HT6 receptor ligands. *J. Med. Chem.* 44(23):3881-3895.

\* cited by examiner

TETRACYCLIC ARYLSULFONYL INDOLES HAVING SEROTONIN RECEPTOR AFFINITY USEFUL AS THERAPEUTIC AGENTS, PROCESS FOR THEIR PREPARATION AND PHARMACEUTICAL COMPOSITIONS CONTAINING THEM

FIELD OF INVENTION

The present invention relates to novel tetracyclic arylsulfonyl indoles, their derivatives, their analogues, their tautomeric forms, their stereoisomers, their polymorphs, their pharmaceutically acceptable salts, their pharmaceutically acceptable solvates, novel intermediates described herein and pharmaceutically acceptable compositions containing them.

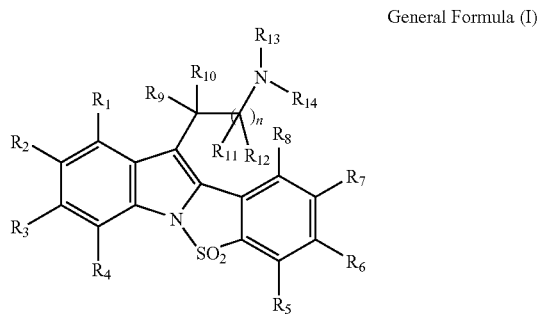

General Formula (I)

The present invention also relates to the process for preparing the compounds of general formula (I), their derivatives, their analogs, their tautomeric forms, their stereoisomers, their geometric forms, their N-oxides, their polymorphs, their pharmaceutically acceptable salts, their pharmaceutically acceptable solvates, novel intermediates described herein and pharmaceutically acceptable compositions containing them.

The compounds of the general formula (I) of this invention are 5-HT (Serotonin) ligands e.g. agonists or antagonists. Thus, compounds of general formula (I) of this invention are useful for treating diseases wherein modulation of 5-HT (Serotonin) activity is desired. Specifically, the compounds of this invention are useful in the treatment and/or prophylaxis of psychosis, paraphrenia, psychotic depression, mania, schizophrenia, schizophreniform disorders, anxiety, migraine headache, depression, drug addiction, convulsive disorders, personality disorders, hypertension, autism, post-traumatic stress syndrome, alcoholism, panic attacks, obsessive-compulsive disorders and sleep disorders. T The compounds of general formula (I) of this invention are also useful to treat psychotic, affective, vegetative and psychomotor symptoms of schizophrenia and the extrapyramidal motor side effects of other antipsychotic drugs.

The compounds of general formula (I) of this invention are also useful to treat neurodegenerative disorders like Alzheimer's disease, Parkinsonism and Huntington's chorea and chemotherapy-induced vomiting. The compounds of general formula (I) of this invention are also useful in modulation of eating behavior and thus are useful in reducing the morbidity and mortality associated with excess weight

BACKGROUND OF THE INVENTION

Many diseases of the central nervous system are influenced by the adrenergic, the dopaminergic and the serotonergic neurotransmitter systems. Serotonin has been implicated in a number of diseases and conditions, which originate in the central nervous system, these include diseases and conditions related to sleeping, eating, perceiving pain, controlling body temperature, controlling blood pressure, depression, anxiety, schizophrenia and other bodily states. (References: Fuller, R. W., Drugs Acting on Serotonergic Neuronal Systems, Biology of Serotonergic Transmission, John Wiley & Sons Ltd. (1982), 221-247; Boullin D. J., Serotonin in Mental abnormalities (1978), 1, 316; Barchas J. et. al., Serotonin and Behavior (1973)). Serotonin also plays an important role in the peripheral systems, such as the gastrointestinal system, where it has been found to mediate a variety of contractile, secretory and electrophysiologic effects.

Due to the broad distribution of serotonin within the body, there is lot of interest and use, in the drugs that affect serotonergic systems. Particularly, preferred are the compounds which have receptor specific agonism and/or antagonism for the treatment of a wide range of disorders, including anxiety, depression, hypertension, migraine, obesity, compulsive disorders, schizophrenia, autism, neurodegenerative disorders like Alzheimer's disease, Parkinsonism and Huntington's chorea and chemotherapy-induced vomiting (References: Gershon M. D. et. al., The peripheral actions of 5-Hydroxytryptamine (1989), 246; Saxena P. R. et al., Journal of Cardiovascular Pharmacology (1990), supplement 7, 15).

The major classes of serotonin receptors (5-HT$_{1-7}$) contain fourteen to eighteen separate receptors that have been formally classified (References: Glennon et al, Neuroscience and Behavioral Reviews (1990), 14, 35 and Hoyer D. et al, Pharmacol. Rev. (1994), 46, 157-203). Recently discovered information regarding sub-type identity, distribution, structure and function suggests that it is possible to identify novel, sub-type specific agents having improved therapeutic profiles with lesser side effects. The 5-HT$_6$ receptor was identified in 1993 (References: Monsma et al, Mol. Pharmacol. (1993), 43, 320-327 and Ruat M. et al, Biochem. Biophys. Res. Com. (1993), 193, 269-276). Several antidepressants and atypical antipsychotics bind to the 5-HT$_6$ receptor with high affinity and this binding may be a factor in their profile of activities (References: Roth et al, J. Pharm. Exp. Therapeut. (1994), 268, 14031410; Sleight et al, Exp. Opin. Ther. Patents (1998), 8, 1217-1224; Bourson et al, Brit J. Pharmacol. (1998), 125, 1562-1566; Boess et al, Mol. Pharmacol., 1998, 54, 577-583; Sleight et al, Brit. J. Pharmacol. (1998), 124, 556-562). In addition, 5-HT$_6$ receptor has been linked to generalized stress and anxiety states (Reference: Yoshioka et al, Life Sciences (1998), 17/18, 1473-1477). Together these studies and observations suggest that compounds that antagonize the 5-HT$_6$ receptor will be useful in treating various disorders of the central nervous system.

U.S. Pat. Nos. 4,839,377 and 4,855,314 refer to 5-substituted 3-aminoalkyl indoles. The compounds are said to be useful for the treatment of migraine.

British Patent 2,035,310 refers to 3-aminoalkyl-1H-indole-5-thioamides and carboxamides. The compounds are said to be useful in treating hypertension, Raymond's disease and migraine.

European Patent Publication 303,506 refers to 3-polyhydropyridyl-5-substituted-1H-indoles. The compounds are said to have 5-HT$_1$ receptor agonists and vasoconstrictor activity and to be useful in treating migraine. European Patent Publication 354,777 refers to N-piperidinylindolylethyl-alkane sulfonamide derivatives. The compounds are said to be 5-HT$_1$ receptor agonists and have vasoconstrictor activity and are useful in treating cephalic pain.

European Patent Publication 438,230, refers to indole-substituted five-membered heteroaromatic compounds. The compounds are said to have "5HT$_1$-like" receptor agonist activity and to be useful in the treatment of migraine and other disorders for which a selective agonist of these receptors is indicated.

European Patent Publication 313,397 refers to 5-heterocyclic indole derivatives. The compounds are said to have exceptional properties for the treatment and prophylaxis of migraine, cluster headache and headache associated with vascular disorders. These compounds are also said to have exceptional "5-HT$_1$-like" receptor agonism.

International Patent Publication WO 91/18897, refers to 5-heterocyclic indole derivatives. The compounds are said to have exceptional properties for the treatment and prophylaxis of migraine, cluster headache, and headache associated with vascular disorders. These compounds are also said to have exceptional "5-HT$_1$-like" receptor agonism.

European Patent Publication 457,701 refers to aryloxy amine derivatives as having high affinity for 5-HT$_{1D}$ serotonin receptors. These compounds are said to be useful for treating diseases related to serotonin receptor dysfunction, for example, migraine.

European Patent Publication 497,512 A2, refers to a class of imidazole, triazole and tetrazole derivatives which are selective agonists for "5-HT$_1$-like" receptors. These compounds are said to be useful for treating migraine and associated disorders.

International Patent Publication WO 93/00086, describes a series of tetrahydrocarbazole derivatives, as 5-HT$_1$ receptor agonists, useful for the treatment of migraine and related conditions.

International Patent Publication WO 93/23396, refers to fused imidazole and triazole derivatives as 5-HT$_1$ receptor agonists, for the treatment of migraine and other disorders.

Schoeffter P. et al. refer to methyl 4-{4-[4-(1,1,3-trioxo-2H-1,2-benzoisothiazol-2-yl)butyl]-1-piperazinyl}1H-indole-3-carboxylate as a selective antagonist for the 5-HT$_{1A}$ receptor in their paper "SDZ216-525, a selective and potent 5-HT$_{1A}$ receptor antagonist" European Journal of Pharmacology, 244, 251-257 (1993).

International Patent Publication WO 94/06769, refers to 2-substituted-4-piperazine-benzothiophene derivatives that are serotonin 5-HT$_{1A}$ and 5-HT$_{1D}$ receptor agents useful in the treatment of anxiety, depression, migraine, stroke, angina and hypertension.

SUMMARY OF THE INVENTION

The present invention relates to novel tetracyclic arylsulfonyl indoles, their derivatives, their analogues, their tautomeric forms, their stereoisomers, their polymorphs, their pharmaceutically acceptable salts, their pharmaceutically acceptable solvates, novel intermediates described herein and pharmaceutically acceptable compositions containing them.

More particularly, the present invention relates to novel tetracyclic arylsulfonyl indoles of the general formula (I), their derivatives, their analogs, their tautomeric forms, their stereoisomers, their polymorphs, their pharmaceutically acceptable salts, their pharmaceutically acceptable solvates, novel intermediates described herein and pharmaceutically acceptable compositions containing them and use of these compounds in medicine.

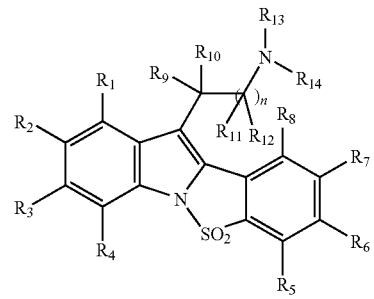

General Formula (I)

wherein $R_1$, $R_2$, $R_3$, $R_4$, $R_5$, $R_6$, $R_7$, $R_8$, $R_9$, $R_{10}$, $R_{11}$ and $R_{12}$ may be same or different and each independently represent hydrogen, halogen, oxo, thio, perhaloalkyl, hydroxy, amino, nitro, cyano, formyl, amidino, guanidino, substituted or unsubstituted groups such as linear or branched ($C_1$-$C_{12}$) alkyl, ($C_2$-$C_{12}$)alkenyl, ($C_2$-$C_{12}$)alkynyl, ($C_3$-$C_7$)cycloalkyl, ($C_3$-$C_7$)cycloalkenyl, bicycloalkyl, bicycloalkenyl, ($C_1$-$C_{12}$) alkoxy, cyclo($C_3$-$C_7$)alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyl, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_5$ and $R_6$ or $R_6$ and $R_7$ or $R_7$ and $R_8$ together with carbon atoms to which they are attached may form a 5, 6, or 7 membered ring, which may further optionally contain one or more double bonds and/or one or more heteroatoms such as the group "Oxygen", "Nitrogen", "Sulfur" or "Selenium" and combinations of double bond and heteroatoms; or $R_9$ and $R_{10}$ or $R_{11}$ and $R_{12}$ together represent double bond attached to "Oxygen" or "Sulfur"; or $R_9$ and $R_{10}$ or $R_{11}$ and $R_{12}$ together with the carbon atoms to which they are attached may form a 3, 4, 5, or 6 membered ring, which may further optionally contain one or more double bonds, and/or one or more heteroatoms such as the group "Oxygen", "Nitrogen", "Sulfur" or "Selenium" and also includes combination of one or more double bonds with "heteroatoms", as above defined.

$R_{13}$ and $R_{14}$ may be same or different and each independently represents hydrogen, substituted or unsubstituted groups such as linear or branched ($C_1$-$C_{12}$)alkyl, ($C_2$-$C_{12}$) alkenyl, ($C_2$-$C_{12}$)alkynyl, ($C_2$-$C_{12}$)alkanoyl ($C_3$-$C_7$)cycloalkyl, ($C_3$-$C_7$)cycloalkenyl, bicycloalkyl, bicycloalkenyl, aryl, aralkyl, heteroaryl, heterocyclylalkyl; optionally $R_{13}$ and $R_{14}$ along with the nitrogen atom, may form a 3, 4, 5, 6 or 7-membered heterocyclic ring, wherein the ring may be further substituted, and it may have either one, two or three double bonds or "additional heteroatoms", as defined above.

"n" is an integer ranging from 1 to 8. It is preferred that n be 1 to 4. The carbon chains which "n" represents may be either linear or branched.

Partial List of Such Compounds of General Formula (I) is as Follows:

6-(2-N,N-Dimethylaminoethyl)benzo[d]isothiazolo[3,2-a]indol-S,S-dioxide;
4-Bromo-6-(2-N,N-dimethylaminoethyl)benzo[d]isothiazolo[3,2-a]indol-S,S-dioxide;
4-Chloro-6-(2-N,N-dimethylaminoethyl)-benzo[d]isothiazolo[3,2-a]indol-S,S-dioxide;
6-(2-N,N-Dimethylaminoethyl)-4-fluorobenzo[d]isothiazolo[3,2-a]indol-S,S-dioxide;
6-(2-N,N-Dimethylaminoethyl)-4-methylbenzo[d]isothiazolo[3,2-a]indol-S,S-dioxide;
6-(2-N,N-Dimethylaminoethyl)-4-methylbenzo[d]isothiazolo[3,2-a]indol-S,S-dioxide hydrochloride salt;
6-(2-N,N-Dimethylaminoethyl)-4-methylbenzo[d]isothiazolo[3,2-a]indol-S,S-dioxide maleate salt;
6-(2-N,N-Dimethylaminoethyl)-4-methylbenzo[d]isothiazolo[3,2-a]indol-S,S-dioxide D,L-malic acid salt;
6-(2-N,N-Dimethylaminoethyl)-4-methylbenzo[d]isothiazolo[3,2-a]indol-S,S-dioxide oxalate salt;
6-(2-N,N-Dimethylaminoethyl)-4-methylbenzo[d]isothiazolo[3,2-a]indol-S,S-dioxide citrate salt;
6-(2-N,N-Dimethylaminoethyl)-4-methoxybenzo[d]isothiazolo[3,2-a]indol-S,S-dioxide;
6-(2-N,N-Dimethylaminoethyl)-8-methoxybenzo[d]isothiazolo[3,2-a]indol-S,S-dioxide;
4-Bromo-6-(2-N,N-dimethylaminoethyl)-8-methoxybenzo[d]isothiazolo[3,2-a]indol-S,S-dioxide;
4-Chloro-6-(2-N,N-dimethylaminoethyl)-8-methoxybenzo[d]isothiazolo[3,2-a]indol-S,S-dioxide;
6-(2-N,N-Dimethylaminoethyl)-4-fluoro-8-methoxybenzo[d]isothiazolo[3,2-a]indol-S,S-dioxide;
6-(2-N,N-Dimethylaminoethyl)-4-methyl-8-methoxybenzo[d]isothiazolo[3,2-a]indol-S,S-dioxide;
6-(2-N,N-Dimethylaminoethyl)-4,8-dimethoxybenzo[d]isothiazolo[3,2-a]indol-S,S-dioxide;
6-(2-N,N-Dimethylaminoethyl)-2-ethylbenzo[d]isothiazolo[3,2-a]indol-S,S-dioxide;
2-Chloro-6-(2-N,N-dimethylaminoethyl)benzo[d]isothiazolo[3,2-a]indol-S,S-dioxide;
2,4-Dichloro-6-(2-N,N-dimethylaminoethyl)-benzo[d]isothiazolo[3,2-a]indol-S,S-dioxide;
2,3-Dichloro-6-(2-N,N-dimethylaminoethyl)-benzo[d]isothiazolo[3,2-a]indol-S,S-dioxide;
5-Chloro-6-(2-N,N-dimethylaminoethyl)-2-methylbenzo[d]isothiazolo[3,2-a]indol-S,S-dioxide;
2,4,5-Trichloro-6-(2-N,N-dimethylaminoethyl)-benzo[d]isothiazolo[3,2-a]indol-S,S-dioxide;
6-(2-N,N-Dimethylaminoethyl)-2,4-difluorobenzo[d]isothiazolo[3,2-a]indol-S,S-dioxide;
6-(2-N,N-dimethylaminoethyl)-4fluoro-8-methylbenzo[d]isothiazolo[3,2-a]indol-S,S-dioxide;
2,4-Difluoro-6-(2-N,N-dimethylaminoethyl)-8-methyl-benzo[d]isothiazolo[3,2-a]indol-S,S-dioxide;
6-(2-N,N-Dimethylaminoethyl)-2-methoxybenzo[d]isothiazolo[3,2-a]indol-S,S-dioxide;
6-(2-N,N-Dimethylaminoethyl)-2,8-dimethoxybenzo[d]isothiazolo[3,2-a]indol-S,S-dioxide;
6-(2-N,N-Dimethylaminoethyl)-8-methylbenzo[d]isothiazolo[3,2-a]indol-S,S-dioxide;
6-(3-N,N-Dimethylamino-1-hydroxyprop-1-yl)benzo[d]isothiazolo[3,2-a]indol-S,S-dioxide;
4-Bromo-6-(3-N,N-Dimethylamino-1-hydroxyprop-1-yl)benzo[d]isothiazolo[3,2-a]indol-S,S-dioxide;
6-(3-N,N-Dimethylamino-1-hydroxyprop-1-yl)-8-methoxy-benzo[d]isothiazolo[3,2-a]indol-S,S-dioxide;
6-(3-N,N-Dimethylamino-1-hydroxyprop-1-yl)-8-methyl-benzo[d]isothiazolo[3,2-a]indol-S,S-dioxide;
4-Bromo(3-N,N-dimethylamino-1-hydroxyprop-1-yl)-8-methoxybenzo[d]isothiazolo[3,2-a]indol-S,S-dioxide;
6-[2-(4-Methylpiperazin-1-yl)ethyl]benzo[d]isothiazolo[3,2-a]indol-S,S-dioxide;
6-[2-Morpholin-4-ylethyl]benzo[d]isothiazolo[3,2-a]indol-S,S-dioxide;
6-(2-Pyrrolidin-1-ylethyl)benzo[d]isothiazolo[3,2-a]indol-S,S-dioxide;
6-(2-Piperidin-1-yl)ethyl]benzo[d]isothiazolo[3,2-a]indol-S,S-dioxide;
4-Bromo[2-morpholin-4-ylethyl]benzo[d]isothiazolo[3,2-a]indol-S,S-dioxide;
4-Bromo-6-(2-pyrrolidin-1-ylethyl)benzo[d]isothiazolo[3,2-a]indol-S,S-dioxide;
4-Bromo-6-[2-(4methylpiperazin-1-yl)ethyl]benzo[d]isothiazolo[3,2-a]indol-S,S-dioxide;
6-(3-(Piperidin-1-yl)-1-hydroxyprop-1-yl)benzo[d]isothiazolo[3,2-a]indol-S,S-dioxide;
6-(3-(Piperidin-1-yl)-1-hydroxyprop-1-yl)-8-methoxybenzo[d]isothiazolo[3,2-a]indol-S,S-dioxide;
4-Bromo-6-(3-(piperidin-1-yl)-1-hydroxyprop-1-yl)benzo[d]isothiazolo[3,2-a]indol-S,S-dioxide;
4-Bromo-6-(3-(piperidin-1-yl)-1-hydroxyprop-1-yl)-8-methoxybenzo[d]isothiazolo[3,2-a]indol-S,S-dioxide;
6-(3-(Pyrrolidin-1-yl)-1-hydroxyprop-1-yl)benzo[d]isothiazolo[3,2-a]indol-S,S-dioxide;
6-(3-(Pyrrolidin-1-yl)-1-hydroxyprop-1-yl)-8-methoxy-benzo[d]isothiazolo[3,2-a]indol-S,S-dioxide;
6-(2-(N,N-Diethylamino)-2-methylethyl)benzo[d]isothiazolo[3,2-a]indol-S,S-dioxide;
6-(2-(N,N-Dimethylamino-1-hydroxy-1-yl)benzo[d]isothiazolo[3,2-a]indol-S,S-dioxide;
4-Bromo-6-(2-(N,N-Dimethylamino-1-hydroxy-1-yl)benzo[d]isothiazolo[3,2-a]indol-S,S-dioxide;
6-(2-(N,N-Dimethylaminoethyl)-2,4-difluoro-8-Methoxy-benzo[d]isothiazolo[3,2-a]indol-S,S-dioxide;
6-(2-(N,N-Dimethylamino-2-methylethyl)benzo[d]isothiazolo[3,2-a]indol-S,S-dioxide;
4-Chloro-6-(2-(N,N-Dimethylaminoethyl)-8-methylbenzo[d]isothiazolo[3,2-a]indol-S,S-dioxide;
8-(2-(N,N-Dimethylaminoethyl)benzo[d]isothiazolo[3,2-a]benzo(g)indol-S,S-dioxide; and its stereoisomers, its N-oxides, its polymorphs, its pharmaceutically acceptable salts and solvates.

The present invention also envisages some useful bio-active metabolites of the compounds of general formula (I).

The compounds of general formula (I) of this invention are useful in the treatment and/or prophylaxis of a condition wherein modulation of 5-HT activity is desired.

The present invention provides for use of the compounds of general formula (I) according to above, for the manufacture of the medicaments for the potential use in the treatment and/or prophylaxis of certain CNS disorders such as, anxiety, depression, convulsive disorders, obsessive-compulsive disorders, migraine headache, cognitive memory disorders e.g. Alzheimer's disease and age-related cognitive decline, ADHD (Attention Deficit Disorder/Hyperactivity Syndrome), personality disorders, psychosis, paraphrenia, psychotic depression, mania, schizophrenia, schizophreniform disorders, withdrawal from drug abuse such as cocaine, ethanol, nicotine and benzodiazepines, panic attacks, sleep disorders (including disturbances of Circadian rhythm) and also disorders associated with spinal trauma and/or head injury such as hydrocephalus. Compounds of the invention are further expected to be of use in the treatment of mild cognitive impairment and other neurodegenerative disorders like Alzheimer's disease, Parkinsonism and Huntington's chorea.

The compounds of the invention are also expected to be of use in the treatment of certain GI (Gastrointestinal) disorders such as IBS (Irritable bowel syndrome) or chemotherapy induced emesis.

The compounds of the invention are also expected to be of use in the modulation of eating behavior and these compounds can also be used to reduce morbidity and mortality associated with the excess weight.

The present invention provides a method for the treatment of a human or a animal subject suffering from certain CNS disorders such as, anxiety, depression, convulsive disorders, obsessive-compulsive disorders, migraine headache, cognitive memory disorders e.g. Alzheimer's disease and age-related cognitive decline, ADHD (Attention Deficit Hyperactivity Disorder), personality disorders, psychosis, paraphrenia, psychotic depression, mania, schizophrenia, schizophreniform disorders, withdrawal from drug abuse such as cocaine, ethanol, nicotine and benzodiazepines, panic attacks, sleep disorders (including disturbances of Circadian rhythm) and also disorders associated with spinal trauma and/or head injury such as hydrocephalus. Compounds of the invention are further expected to be of use in the treatment of mild cognitive impairment and other neurodegenerative disorders like Alzheimer's disease, Parkinsonism and Huntington's chorea.

The present invention also provides a method for modulating 5-HT receptor function desired in certain cases.

The present invention also includes a isotopically-labelled compounds, which are identical to those defined in the general formula (I), but for the fact that one or more atoms are replaced by an atom having an atomic mass or mass number different from the atomic mass or mass number found usually in nature. Examples of isotopes that can be incorporated into compounds of the invention include isotopes of hydrogen, carbon, nitrogen, oxygen, phosphorus, fluorine, chlorine, iodine, bromine and mTecnitium, exemplified by $^2H$, $^3H$, $^{11}C$, $^{13}C$, $^{14}C$, $^{13}N$, $^{15}N$, $^{15}O$, $^{18}F$, $^{99m}Tc$, $^{31}P$, S, $^{123}I$ and $^{125}I$. Compounds of present invention and pharmaceutically acceptable salts and prodrugs of said compounds that contain the aforementioned isotopes and/or other isotopes of other atoms are within the scope of this invention.

Isotopically labelled compounds of the present invention are useful in drug and/or substrate tissue distribution and target occupancy assays. For example, isotopically labelled compounds are particularly useful in SPECT (single photon emission computed tomography) and in PET (positron emission tomography).

An effective amount of a compound of general formula (I) or its salt is used for producing medicaments of the present invention, along with conventional pharmaceutical auxiliaries, carriers and additives.

The present invention also relates to a pharmaceutical composition for treating and/or prophylaxis of disorders, a condition wherein modulation of 5-HT is desired in a mammal, preferably a human, comprising:
  a. a pharmaceutically acceptable carrier
  b. a compound of general formula (I) as defined above, and
  c. a 5HT re-uptake inhibitor, or its pharmaceutically acceptable salt;
wherein the amounts of each active compound (a compound of general formula (I) and a 5HT re-uptake inhibitor), is such that the combination is effective in treating such a condition.

The present invention also relates to a method of treatment and/or prophylaxis of disorders, a condition wherein modulation of 5-HT is desired in a mammal, preferably a human, comprising:
  a. a pharmaceutically acceptable carrier
  b. a compound of general formula (I) as defined above, and
  c. a 5-HT re-uptake inhibitor, or its pharmaceutically acceptable salt;
wherein the amounts of each active compound (a compound of general formula (I) and a 5HT re-uptake inhibitor), is such that the combination is effective in treating such a condition.

The present invention also relates to a process for the preparation of the above said novel compounds, their derivatives, their analogues, their tautomeric forms, their stereoisomers, their geometric forms, their N-oxides, their polymorphs, their pharmaceutically acceptable salts, their pharmaceutically acceptable solvates, novel intermediates described herein and pharmaceutical compositions containing them.

DETAILED DESCRIPTION OF THE INVENTION

The present invention relates to novel tetracyclic arylsulfonyl indoles, their derivatives, their analogues, their tautomeric forms, their stereoisomers, their polymorphs, their pharmaceutically acceptable salts, their pharmaceutically acceptable solvates, novel intermediates described herein and pharmaceutically acceptable compositions containing them.

More particularly, the present invention relates to novel tetracyclic arylsulfonyl indoles of the general formula (I), their derivatives, their analogs, their tautomeric forms, their stereoisomers, their polymorphs, their pharmaceutically acceptable salts, their pharmaceutically acceptable solvates, novel intermediates described herein and pharmaceutically acceptable compositions containing them and use of these compounds in medicine.

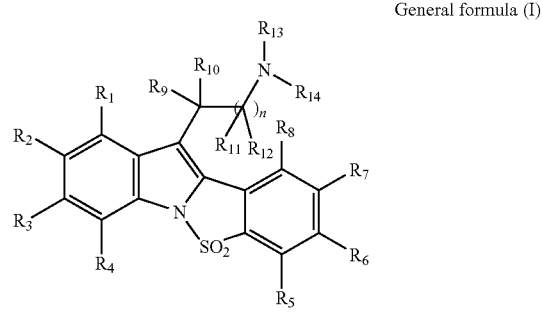

General formula (I)

wherein $R_1$, $R_2$, $R_3$, $R_4$, $R_5$, $R_6$, $R_7$, $R_8$, $R_9$, $R_{10}$, $R_{11}$ and $R_{12}$ may be same or different and each independently represent hydrogen, halogen, oxo, thio, perhaloalkyl, hydroxy, amino, nitro, cyano, formyl, amidino, guanidino, substituted or unsubstituted groups such as linear or branched ($C_1$-$C_{12}$) alkyl, ($C_2$-$C_{12}$)alkenyl, ($C_2$-$C_{12}$)alkynyl, ($C_3$-$C_7$)cycloalkyl, ($C_3$-$C_7$)cycloalkenyl, bicycloalkyl, bicycloalkenyl, ($C_1$-$C_{12}$) alkoxy, cyclo($C_3$-$C_7$)alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_5$ and $R_6$ or $R_6$ and $R_7$ or $R_7$ and $R_8$ together with carbon atoms to which they are attached may form a 5, 6, or 7 membered ring, which may further optionally contain one or more double bonds and/or one or more heteroatoms such as the group "Oxygen", "Nitrogen", "Sulfur" or "Selenium" and combinations of double bond and heteroatoms; or $R_9$ and $R_{10}$ or $R_{11}$ and $R_{12}$ together represent double bond attached to "Oxygen" or "Sulfur"; or $R_9$ and $R_{10}$ or $R_{11}$ and $R_{12}$ together with the carbon atoms to which they are attached may form a 3, 4, 5, or 6 membered ring, which may further optionally contain one or more double bonds, and/or one or more heteroatoms such as the group "Oxygen", "Nitrogen", "Sulfur" or "Selenium" and also includes combination of one or more double bonds with "heteroatoms", as above defined.

$R_{13}$ and $R_{14}$ may be same or different and each independently represents hydrogen, substituted or unsubstituted groups such as linear or branched $(C_1-C_{12})$alkyl, $(C_2-C_{12})$alkenyl, $(C_2-C_{12})$alkynyl, $(C_2-C_{12})$alkanoyl $(C_3-C_7)$cycloalkyl, $(C_3-C_7)$cycloalkenyl, bicycloalkyl, bicycloalkenyl, aryl, aralkyl, heteroaryl, heterocyclylalkyl; optionally $R_{13}$ and $R_{14}$ along with the nitrogen atom, may form a 3, 4, 5, 6 or 7-membered heterocyclic ring, wherein the ring may be further substituted, and it may have either one, two or three double bonds or "additional heteroatoms", as defined above.

"n" is an integer ranging from 1 to 8. It is preferred that n be 1 to 4. The carbon chains which "n" represents may be either linear or branched.

Suitable groups represented by $R_1$, $R_2$, $R_3$, $R_4$, $R_5$, $R_6$, $R_7$, $R_8$, $R_9$, $R_{10}$, $R_{11}$ and $R_{12}$ may be a halogen atom such as fluorine, chlorine, bromine or iodine; perhaloalkyl particularly perhalo$(C_1-C_6)$alkyl such as fluoromethyl, difluoromethyl, trifluoromethyl, trifluoroethyl, fluoroethyl, difluoroethyl and the like; substituted or unsubstituted $(C_1-C_{12})$alkyl group, linear or branched $(C_1-C_8)$alkyl group, such as methyl, ethyl, n-propyl, iso-propyl, n-butyl, iso-butyl, t-butyl, n-pentyl, iso-pentyl, hexyl, iso-hexyl, heptyl, octyl and the like; substituted or unsubstituted $(C_2-C_{12})$alkenyl group such as ethylene, n-propylene pentenyl, hexenyl, heptynyl, heptadienyl and the like; $(C_2-C_{12})$alkynyl substituted or unsubstituted $(C_2-C_{12})$alkynyl group such as acetylene and the like; cyclo$(C_3-C_7)$alkyl group such as cyclopropyl, cyclobutyl, cyclopentyl, cyclohexyl, cycloheptyl, the cycloalkyl group may be substituted; cyclo$(C_3-C_7)$alkenyl group such as cyclopentenyl, cyclohexenyl, cycloheptynyl, cycloheptadienyl, cycloheptatrienyl and the like, the cycloalkenyl group may be substituted; $(C_1-C_{12})$alkoxy, especially, $(C_1-C_6)$alkoxy group such as methoxy, ethoxy, propyloxy, butyloxy, iso-propyloxy and the like, which may be substituted; cyclo$(C_3-C_7)$ alkoxy group such as cyclopropyloxy, cyclobutyloxy, cyclopentyloxy, cyclohexyloxy, cycloheptyloxy and the like, the cycloalkoxy group may be substituted; aryl group such as phenyl or naphthyl, the aryl group may be substituted; aralkyl group such as benzyl, phenethyl, $C_6H_5CH_2CH_2CH_2$, naphthylmethyl and the like, the aralkyl group may be substituted and the substituted aralkyl is a group such as $CH_3C_6H_4CH_2$, Hal-$C_6H_4CH_2$, $CH_3OC_6H_4CH_2$, $CH_3OC_6H_4CH_2CH_2$ and the like; aralkoxy group such as benzyloxy, phenethyloxy, naphthylmethyloxy, phenylpropyloxy and the like, the aralkoxy group may be substituted; heterocyclyl groups such as aziridinyl, pyrrolidinyl, morpholinyl, piperidinyl, piperazinyl and the like, the heterocyclyl group may be substituted; heteroaryl group such as pyridyl, thienyl, furyl, pyrrolyl, oxazolyl, imidazolyl, oxadiazolyl, tetrazolyl, benzopyranyl, benzofuranyl and the like, the heteroaryl group may be substituted; heterocyclo$(C_1-C_6)$alkyl, such as pyrrolidinylalkyl, piperidinylalkyl, morpholinylalkyl, thiomorpholinylalkyl, oxazolinylalkyl and the like, the heterocyclo$(C_1-C_6)$alkyl group may be substituted; heteroaralkyl group such as furanylmethyl, pyridinylmethyl, oxazolylmethyl, oxazolylethyl and the like, the heteroaralkyl group may be substituted; heteroaryloxy, heteroaralkoxy, heterocycloalkoxy, wherein heteroaryl, heteroaralkyl, heterocycloalkyl and heterocyclylalkyl moieties are as defined earlier and may be substituted; acyl groups such as acetyl, propionyl or benzoyl, the acyl group may be substituted; acyloxy group such as $CH_3COO$, $CH_3CH_2COO$, $C_6H_5COO$ and the like which may optionally be substituted, acylamino group such as $CH_3CONH$, $CH_3CH_2CONH$, $C_3H_7CONH$, $C_6H_5CONH$ which may be substituted, $(C_1-C_6)$monoalkylamino group such as $CH_3NH$, $C_2H_5NH$, $C_3H_7NH$, $C_6H_{13}NH$ and the like, which may be substituted, $(C_1-C_6)$dialkylamino group such as $N(CH_3)_2$, $CH_3(C_2H_5)N$ and the like, which may be substituted; arylamino group such as $C_6H_5NH$, $CH_3(C_6H_5)N$, $C_6H_4(CH_3)$NH, $NH-C_6H_4$-Hal and the like, which may be substituted; arylalkylamino group such as $C_6H_5CH_2NH$, $C_6H_5CH_2CH_2NH$, $C_6H_5CH_2NCH_3$ and the like, which may be substituted; hydroxy$(C_1-C_6)$alkyl which may be substituted, amino$(C_1-C_6)$alkyl which may be substituted; mono$(C_1-C_6)$alkylamino$(C_1-C_6)$alkyl, di$(C_1-C_6)$alkylamino$(C_1-C_6)$alkyl group which may be substituted, alkoxyalkyl group such as methoxymethyl, ethoxymethyl, methoxyethyl, ethoxyethyl and the like, which may be substituted; aryloxyalkyl group such as $C_6H_5OCH_2$, $C_6H_5OCH_2CH_2$, naphthyloxymethyl and the like, which may be substituted; aralkoxyalkyl group such as $C_6H_5CH_2OCH_2$, $C_6H_5CH_2OCH_2CH_2$ and the like, which may be substituted; $(C_1-C_6)$alkylthio, thio$(C_1-C_6)$alkyl which may be substituted, alkoxycarbonylamino group such as $C_2H_5OCONH$, $CH_3OCONH$ and the like which may be substituted; aryloxycarbonylamino group as $C_6H_5OCONH$, $C_6H_5OCONCH_3$, $C_6H_5OCONC_2H_5$, $C_6H_4CH_3OCONH$, $C_6H_4(OCH_3)OCONH$ and the like which may be substituted; aralkoxycarbonylamino group such $C_6H_5CH_2OCONH$, $C_6H_5CH_2CH_2OCONH$, $C_6H_5CH_2OCON(CH_3)$, $C_6H_5OCON(C_2H_5)$, $C_6H_4CH_3CH_2OCONH$, $C_6H_4OCH_3CH_2OCONH$ and the like, which may be substituted; aminocarbonylamino group; $(C_1-C_6)$alkylaminocarbonylamino group, di$(C_1-C_6)$alkylaminocarbonylamino group; $(C_1-C_6)$alkylamidino group, $(C_1-C_6)$alkylguanidino, di$(C_1-C_6)$alkylguanidino groups, hydrazino and hydroxylamino groups; carboxylic acid or its derivatives such as amides, like $CONH_2$, alkylaminocarbonyl like $CH_3NHCO$, $(CH_3)_2NCO$, $C_2H_5NHCO$, $(C_2H_5)_2NCO$, arylaminocarbonyl like PhNHCO, NapthylNHCO and the like, aralkylaminocarbonyl such as $PhCH_2NHCO$, $PhCH_2CH_2NHCO$ and the like, heteroarylaminocarbonyl and heteroaralkylamino carbonyl groups where the heteroaryl groups are as defined earlier, heterocyclylaminocarbonyl where the heterocyclyl group is as defined earlier, carboxylic acid derivatives such as esters, wherein the ester moieties are alkoxycarbonyl groups such as unsubstituted or substituted phenoxycarbonyl, naphthyloxycarbonyl and the like; aralkoxycarbonyl group such as benzyloxycarbonyl, phenethyloxycarbonyl, naphthylmethoxycarbonyl and the like, heteroaryloxycarbonyl, heteroaralkoxycarbonyl, wherein the heteroaryl group is as defined earlier, heterocycloxycarbonyl where heterocycle is as defined earlier and these carboxylic acid derivatives may be substituted; sulfonic acid or its derivatives such as $SO_2NH_2$, $SO_2NHCH_3$, $SO_2N(CH_3)_2$, $SO_2NHCF_3$, $SO_2NHCO(C_1-C_6)$alkyl, $SO_2NHCO$aryl where the aryl group is as defined earlier and the sulfonic acid derivatives may be substituted; phosphoric acid and its derivatives such as $P(O)(OH)_2$, $P(O)(OC_1-C_6alkyl)_2$, $P(O)(O-aryl)_2$ and the like.

Suitable cyclic structures formed by the two adjacent groups like $R_1$ and $R_2$ or $R_2$ and $R_3$ or $R_3$ and $R_4$ or $R_5$ and $R_6$ or $R_6$ and $R_7$ or $R_7$ and $R_8$ together with carbon atoms to which they are attached may form a five or a six membered ring, which may further optionally contain one or more double bonds and/or one or more heteroatoms such as the group "Oxygen", "Nitrogen", "Sulfur" or "Selenium" or a combination of one or more double bonds and hetero atoms, the cyclic structures may be optionally substituted phenyl, naphthyl, pyridyl, furanyl, thienyl, pyrrolyl, imidazolyl, pyrimidinyl, pyrazinyl and the like. Suitable substituents on the cyclic structure formed by $R_1$ and $R_2$ or $R_2$ and $R_3$ or $R_3$ and $R_4$ or $R_5$ and $R_6$ or $R_8$ and $R_7$ or $R_7$ and $R_8$ together with the adjacent carbon atoms to which they are attached include oxo, hydroxy, halogen atom such as chlorine, bromine and iodine; nitro, cyano, amino, formyl, $(C_1-C_3)$alkyl, $(C_1-C_3)$alkoxy, thioalkyl, alkylthio phenyl or benzyl groups.

$R_{13}$ and $R_{14}$ represents hydrogen, substituted or unsubstituted linear or branched $(C_1-C_{12})$alkyl such as methyl, ethyl, n-propyl, iso-propyl, n-butyl, iso-butyl, pentyl, hexyl, octyl and the like; $(C_2-C_{12})$alkanoyl such as acetyl, propanoyl and the like; aryl group such as phenyl or naphthyl, the aryl group may be substituted; cyclo$(C_3-C_7)$alkyl group such as cyclopropyl, cyclobutyl, cyclopentyl, cyclohexyl, cycloheptyl, the cycloalkyl group may be substituted; the aralkyl group may be substituted and the substituted aralkyl is a group such as $CH_3C_6H_4CH_2$, Hal-$C_6H_4CH_2$, $CH_3OC_6H_4CH_2$, $CH_3OC_6H_4CH_2CH_2$ and the like; $(C_3-C_7)$cycloheteroalkyl with heteroatoms like "Oxygen", "Nitrogen", "Sulfur" or "Selenium" optionally containing one or two, multiple bonds such as double or triple bonds. Suitable hetero cyclic rings formed between $R_{13}$ and $R_{14}$ along with "Nitrogen atom" be such as pyrrolyl, pyrrolidinyl, piperidinyl, pyridine, 1,2,3, 4Tetrahydro-pyridine, imidazolyl, pyrimidinyl, pyrazinyl, piperazinyl, diazolinyl and the like; the heterocyclyl group may be substituted; heteroaryl group such as pyridyl, imidazolyl, tetrazolyl and the like, the heteroaryl group may be substituted; heterocyclo$(C_1-C_6)$alkyl, such as pyrrolidinealkyl, piperidinealkyl, morpholinealkyl, thiomorpholinealkyl, oxazolinealkyl and the like, the heterocyclo$(C_1-C_6)$ alkyl group may be substituted; heteroaralkyl group such as furanmethyl, pyridinemethyl, oxazolemethyl, oxazolethyl and the like, the heteroaralkyl group may be substituted; heteroaryloxy, heteroaralkoxy, heterocycloalkoxy, wherein heteroaryl, heteroaralkyl, heterocycloalkyl and heterocyclylalkyl moieties are as defined earlier and may be further substituted.

In the case of the compounds of general formula (I) having an asymmetric carbon atom the present invention relates to the D-form, the L-form and D,L-mixtures and in the case of a number of asymmetric carbon atoms, the diastereomeric forms and the invention extends to each of these stereoisomeric forms and to mixtures thereof including racemates. Those compounds of general formula (I) which have an asymmetric carbon and as a rule are obtained as racemates can be separated one from the other by the usual methods, or any given isomer may be obtained by stereospecific or asymmetric synthesis. However, it is also possible to employ an optically active compound from the start, a correspondingly optically active or diastereomeric compound then being obtained as the final compound.

In the case of the compounds of general formula (I), where tautomerism may exist, the present invention relates to all of the possible tautomeric forms and the possible mixture thereof.

In the case of the compounds of general formula (I) containing geometric isomerism the present invention relates to all of these geometric isomers.

Suitable pharmaceutically acceptable acid addition salts of compounds of the general formula (I) can be prepared of the aforementioned base compounds of this invention are those which form non-toxic acid addition salts, includes, salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benezenesulfonate, p-tolunesulfonate, palmoate and oxalate.

Suitable pharmaceutically acceptable base addition salts of compounds of the general formula (I) can be prepared of the aforementioned acid compounds of this invention are those which form non-toxic base addition salts, includes, salts containing pharmaceutically acceptable cations, such as lithium, sodium, potassium, calcium and magnesium, salts of organic bases such as lysine, arginine, guanidine, diethanolamine, choline, tromethamine and the like; ammonium or substituted ammonium salts.

Pharmaceutically acceptable salts forming part of this invention are intended to define but not limited to the above list.

In addition, pharmaceutically acceptable salts of the compound of formula (I) can be obtained by converting derivatives which have tertiary amino groups into the corresponding quaternary ammonium salts in the methods known in the literature by using quarternizing agents. Possible quarternizing agents are, for example, alkyl halides such as methyl iodide, ethyl bromide and n-propyl chloride, including arylalkyl halides such as benzyl chloride or 2-phenylethyl bromide.

In the addition to pharmaceutically acceptable salts, other salts are included in the invention. They may serve as intermediates in the purification of the compounds, in the preparation of other salts, or in the identification and characterization of the compounds or intermediates.

The pharmaceutically acceptable salts of compounds of formula (I) may exists as solvates, such as with water, methanol, ethanol, dimethylformamide, ethyl acetate, and the like. Mixtures of such solvates can also be prepared. The source of such solvate can be from the solvent of crystallization, inherent in the solvent preparation or crystallization, or adventitious to such solvent. Such solvates are within the scope of this invention.

The invention also encompasses the pharmaceutically acceptable prodrugs of the compounds of the formula (I). A prodrug is a drug which has been chemically modified and may be biologically in-active at the site of action, but which may be degraded or modified by one or more enzymatic or other in-vivo processes to the parent form. This prodrug should have a different pharmacokinetic profile than the parent, enabling easier absorption across the mucosal epithelium, better salt formation, or solubility, and/or improved systemic stability (an increase in the plasma half-life, for example). Typically, such chemical modifications include the following:

1. ester or amide derivatives which may be cleaved by esterases or lipases;
2. peptides which may be recognized by specific or non-specific proteases; or
3. derivatives that accumulate at a site of action through membrane selection of a prodrug from or a modified prodrug form; or any combination of 1 to 3, above.

Conventional procedures for the selection and preparation of suitable prodrug derivatives are described, for example, in H. Bundgard, Design of prodrugs, (1985).

Compounds of general formula (I) can be prepared by any of the methods described below. The present invention also provides processes for preparing compounds of general formula (I) as defined above, their derivatives, their analogs, their tautomeric forms, their stereoisomers, their geometric forms, their polymorphs, their pharmaceutically acceptable salts and their pharmaceutically acceptable solvates, novel intermediates described herein, where $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and "n" are as defined previously can be prepared by any of the methods described below:

Scheme-1:

Compounds of general formula (I), may be prepared by cyclizing a novel intermediate of formula (II) given below,

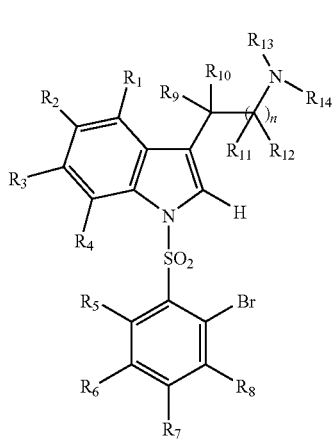

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and "n" are as defined previously, using a Pd(0) or Pd (II) derivative as a catalyst, for example tetrakis triphenylphosphine palladium, (Bis-tri-o-tolylphosphine) palladium and the like; and thereafter if necessary:
  i) converting a compound of the formula (I) into another compound of the formula (I); and/or
  ii) removing any protecting groups; and/or
  iii) forming a pharmaceutically acceptable salt, solvate, polymorph or prodrug thereof.

This cyclization reaction can be achieved using variety of Palladium catalysts. The reaction may be affected in the presence of a base such as $CH_3COOK$. This reaction may be carried out in the presence of solvents such as THF, DMF, DMSO, DMA, DME, acetone and the like and preferably using Dimethylacetamide. The inert atmosphere may be maintained by using inert gases such as $N_2$, Ar or He. The reaction temperature may range from 50° C. to 200° C. based on the choice of solvent and preferably at a temperature of 160° C. The duration of the reaction may range from 1 to 24 hours, preferably from 10 to 20 hours.

Scheme-2:

Compounds of general formula (I), may be prepared by reacting a compound of formula (III) given below,

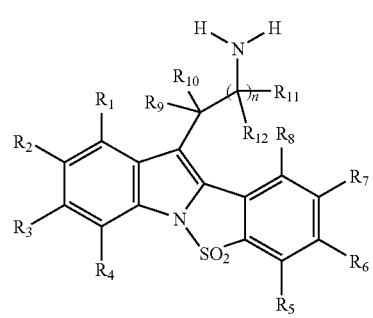

wherein $R_1$, $R_2$, $R_3$, $R_4$, $R_5$, $R_6$, $R_7$, $R_8$, $R_9$, $R_{10}$, $R_{11}$, $R_{12}$ and "n" are as defined previously, with a suitable alkylating agent such as $R_{13}X$ or $R_{14}X$ or $XR_{13}R_{14}X$ in successive steps or in one step, wherein X is good leaving group such as halogen, hydroxyl and the like.

The reaction is preferably carried in an organic solvent inert to the conditions of the reaction, such as acetone, THF or DMF and the like or mixtures thereof. The inert atmosphere may be maintained by using inert gases such as $N_2$, Ar or He. The reaction may be affected in the presence of a base such as $K_2CO_3$, $Na_2CO_3$, TEA or mixtures thereof. The reaction temperature may range from 20° C. to 200° C. based on the solvent employed and preferably at a temperature in the range from 30° C. to 150° C. The duration of the reaction may range from 1 to 24 hours, preferably from 2 to 6 hours.

Scheme-3:

Compounds of general formula (I), may be prepared by reacting a compound of formula (IV) given below,

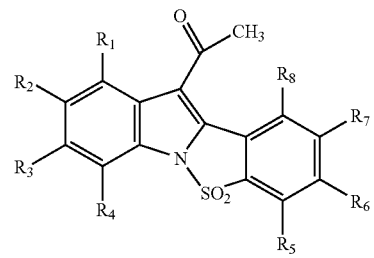

wherein $R_1$, $R_2$, $R_3$, $R_4$, $R_5$, $R_6$, $R_7$, $R_8$ and "n" are as defined previously, with formaldehyde and a compound of formula (V) given below,

wherein $R_{13}$ and $R_{14}$ are as defined earlier.

The above reaction is preferably carried out at a temperature of 50° C. to 150° C. The formaldehyde can be in the form of as aqueous solution i.e. 40% formalin solution, or a polymeric form of formaldehyde such as paraformaldehyde or trioxymethylene. When such polymeric forms are used, a molar excess of mineral acid, for example hydrochloric acid, is added to regenerate the free aldehyde from the polymer. The reaction is preferably carried in an organic solvent inert to the conditions of the reaction, such as methanol, ethanol or 3-methylbutanol and the like or a mixture thereof, and preferably using either acetone or DMF. The inert atmosphere may be maintained by using inert gases such as $N_2$, Ar or He. The reaction temperature may range from 20° C. to 150° C. based on the choice of solvent and preferably at a temperature in the range from 30° C. to 100° C. The duration of the reaction may range from 1 to 24 hours, preferably from 2 to 6 hours.

Scheme-4:

Compounds of general formula (I), may be prepared from another compound of formula (I) containing —C(=O) group/s in the side chain, by known methods of reduction to the corresponding —C(OH,H) or —C(H,H) compound.

Novel intermediates of general formula (II), their stereoisomers and their salts, represented as given below,

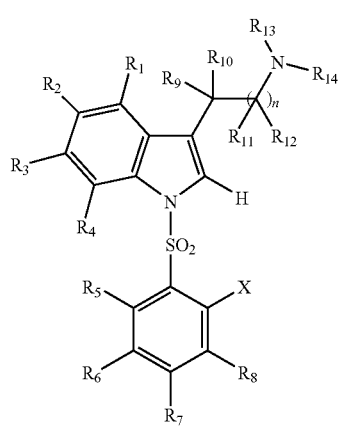

(II)

wherein X is halogen such chloro, bromo or iodo.

$R_1$, $R_2$, $R_3$, $R_4$, $R_5$, $R_6$, $R_7$, $R_8$, $R_9$, $R_{10}$, $R_{11}$ and $R_{12}$ may be same or different and each independently represent hydrogen, halogen, oxo, thio, perhaloalkyl, hydroxy, amino, nitro, cyano, formyl, amidino, guanidino, substituted or unsubstituted groups such as linear or branched ($C_1$-$C_{12}$)alkyl, ($C_2$-$C_{12}$)alkenyl, ($C_2$-$C_{12}$)alkynyl, ($C_3$-$C_7$)cycloalkyl, ($C_3$-$C_7$)cycloalkenyl, bicycloalkyl, bicycloalkenyl, ($C_1$-$C_{12}$)alkoxy, cyclo($C_3$-$C_7$)alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_5$ and $R_6$ or $R_6$ and $R_7$ or $R_7$ and $R_8$ together with carbon atoms to which they are attached may form a 5, 6, or 7 membered ring, which may further optionally contain one or more double bonds and/or one or more heteroatoms such as the group "Oxygen", "Nitrogen", "Sulfur" or "Selenium" and combinations of double bond and heteroatoms; or $R_9$ and $R_{10}$ or $R_{11}$ and $R_{12}$ together represent double bond attached to "Oxygen" or "Sulfur"; or $R_9$ and $R_{10}$ or $R_{11}$ and $R_{12}$ together with the carbon atoms to which they are attached may form a 3, 4, 5, or 6 membered ring, which may further optionally contain one or more double bonds and/or one or more heteroatoms such as the group "Oxygen", "Nitrogen", "Sulfur" or "Selenium" and also includes combination of one or more double bonds with "heteroatoms", as above defined.

$R_{13}$ and $R_{14}$ may be same or different and each independently represents hydrogen, substituted or unsubstituted groups such as linear or branched ($C_1$-$C_{12}$)alkyl, ($C_2$-$C_{12}$)alkenyl, ($C_2$-$C_{12}$)alkynyl, ($C_2$-$C_{12}$)alkanoyl ($C_3$-$C_7$)cycloalkyl, ($C_3$-$C_7$)cycloalkenyl, bicycloalkyl, bicycloalkenyl, aryl, aralkyl, heteroaryl, heterocyclylalkyl; optionally $R_{13}$ and $R_{14}$ along with the nitrogen atom, may form a 3, 4, 5, 6 or 7-membered heterocyclic ring, wherein the ring may be further substituted, and it may have either one, two or three double bonds or "additional heteroatoms", as defined above.

"n" is an integer ranging from 1 to 8. It is preferred that n be 1 to 4. The carbon chains which "n" represents may be either linear or branched.

The present invention also provides processes for preparing the novel intermediate represented by the general formula (II).

Route-1: Compounds of general formula (II), may be prepared by reacting a compound of formula (VI) given below,

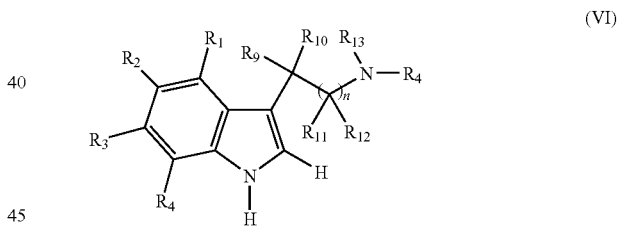

(VI)

where $R_1$, $R_2$, $R_3$, $R_4$, $R_9$, $R_{10}$, $R_{11}$, $R_{12}$, $R_{13}$ and $R_{14}$ are as defined in relation to formula (I); with a compound of formula (VII)

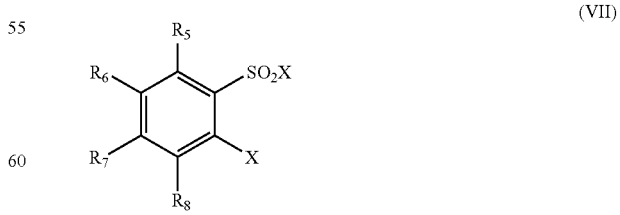

(VII)

where $R_5$, $R_6$, $R_7$ and $R_8$ are as defined in relation to formula (I) and X is a halogen, preferably chloro, bromo or iodo.

This reaction may be carried out in the presence of solvents such as THF, DMF, DMSO, DME, acetone and the like and preferably using either acetone or DMF. The inert atmosphere may be maintained by using inert gases such as N$_2$, Ar or He. The reaction may be affected in the presence of a base such as K$_2$CO$_3$, Na$_2$CO$_3$, NaH, KH or mixtures thereof. The reaction temperature may range from 20° C. to 150° C. based on the choice of solvent and preferably at a temperature in the range from 30° C. to 100° C. The duration of the reaction may range from 1 to 24 hours, preferably from 2 to 6 hours. (Reference: Bio Org. Med Chem. 2000.10, 2295-2299).

Preferably the substituents selected for the compounds of formula (VI) and (VII) are either not affected by the reaction conditions or else the sensitive groups are protected using suitable groups.

Compounds of formula (VI) are commercially available, or they may be prepared by conventional methods or by modification, using known processes, of commercially available compounds of formula (VI). PCT patent application WO 02/078693 also provides methods to prepare variously substituted indoles as well as tryptamines and is incorporated herein by reference.

Route-2: Compounds of general formula (II) may be prepared by the following route

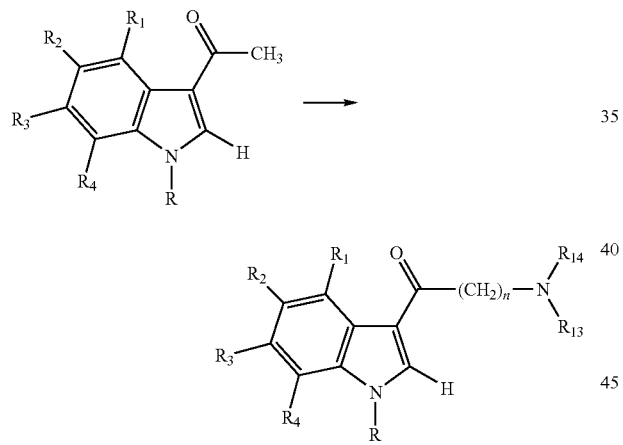

wherein R$_1$, R$_2$, R$_3$, R$_4$, R$_{11}$, R$_{12}$, R$_{13}$, R$_{14}$ and n (=2) are as defined in relation to formula (I); R represents either of hydrogen or a group such as,

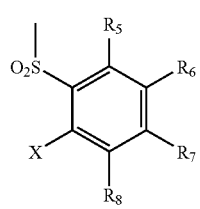

wherein X is halogen such as chloro, bromo or iodo; R$_5$, R$_6$, R$_7$ and R$_8$ are as defined earlier; in presence of amine hydrochloride and formaldehyde.

The above reaction is preferably carried out at a temperature of 50° C. to 150° C. The formaldehyde can be in the form of as aqueous solution i.e. 40% formalin solution, or a polymeric form of formaldehyde such as paraformaldehyde or trioxymethylene. When such polymeric forms are used, a molar excess, of mineral acid, for example hydrochloric acid, is added to regenerate the free aldehyde from the polymer. The reaction is preferably carried in an organic solvent inert to the conditions of the reaction, such as methanol, ethanol or 3-methylbutanol and the like or a mixture thereof. The inert atmosphere may be maintained by using inert gases such as N$_2$, Ar or He. The reaction temperature may range from 20° C. to 150° C. based on the choice of solvent and preferably at a temperature in the range from 30° C. to 100° C. The duration of the reaction may range from 1 to 24 hours, preferably from 2 to 6 hours.

Route-3: Compounds of general formula (II) may be prepared reducing another compound of formula (II) as follows,

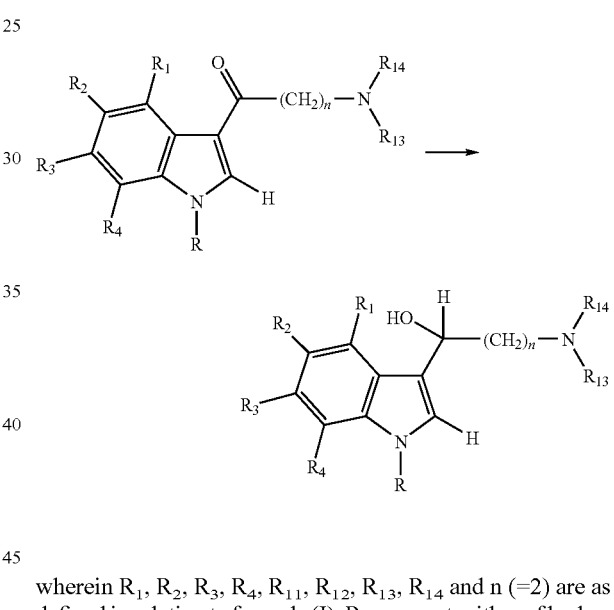

wherein R$_1$, R$_2$, R$_3$, R$_4$, R$_{11}$, R$_{12}$, R$_{13}$, R$_{14}$ and n (=2) are as defined in relation to formula (I); R represents either of hydrogen or a group such as,

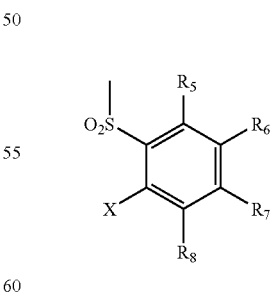

wherein X is halogen such as chloro, bromo or iodo; R$_5$, R$_6$, R$_7$ and R$_8$ are as defined earlier; by use of known various methods of either catalytic (for example, palladium/carbon), chemical (for example, sodium borohydride) or enzymatic reduction.

Route-4: Compounds of general formula (II) may be prepared by the following route

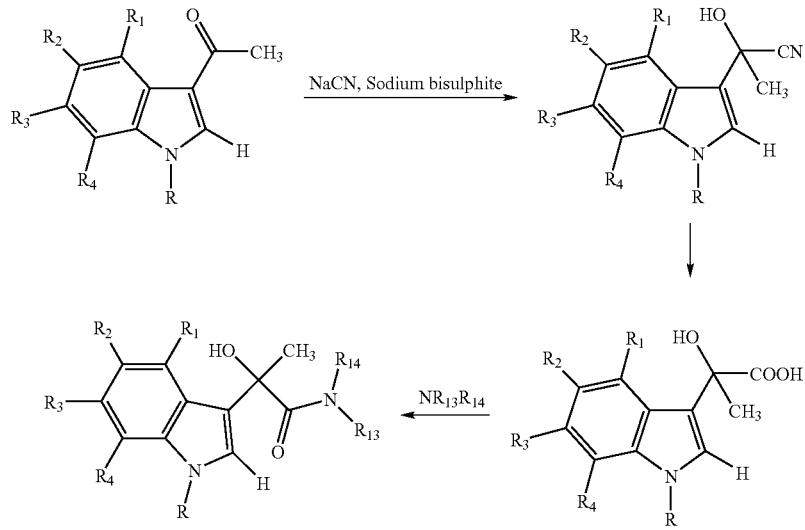

wherein $R_1, R_2, R_3, R_4, R_{11}, R_{12}, R_{13}, R_{14}$ and n are as defined in relation to formula (I); R represents either of hydrogen or a group such as,

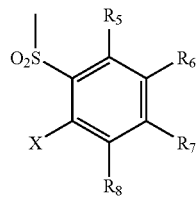

wherein X is halogen such as chloro, bromo or iodo; $R_5$, $R_6$, $R_7$ and $R_8$ are as defined earlier. The first step is well-known strecker reaction, which is followed by conversion of cyano to acid and lastly acid to amide.

The first step involves addition of aqueous solution of sodium bisulfite in the presence of sodium cyanide in a suitable aqueous solvent. The latter two conversions are very-well documented in the literature.

Route-5: Compounds of general formula (II) may be prepared by the following route

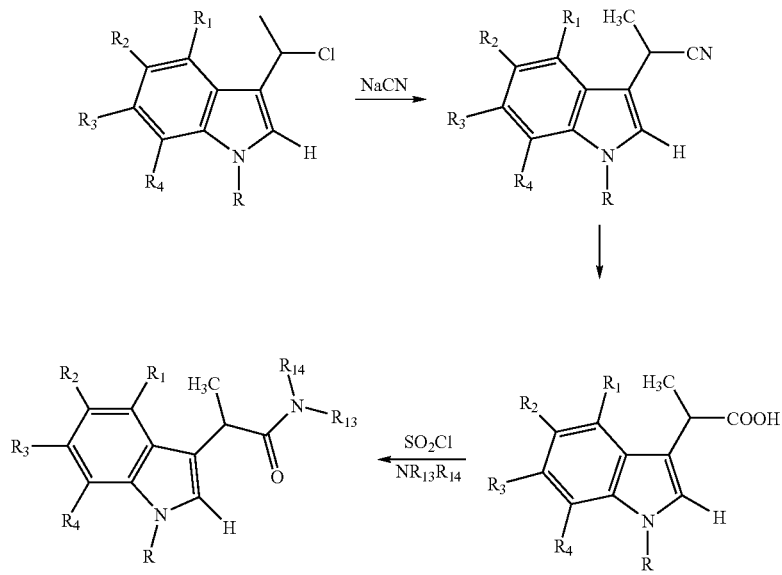

wherein $R_1, R_2, R_3, R_4, R_{11}, R_{12}, R_{13}, R_{14}$ and n are as defined in relation to formula (I); R represents either of hydrogen or a group such as,

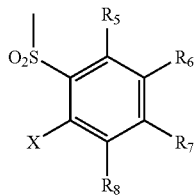

wherein X is halogen such as chloro, bromo or iodo; $R_5, R_6, R_7$ and $R_8$ are as defined earlier. The first step is well-known conversion of chloro to cyano, which is followed by conversion of cyano to acid and lastly acid to amide.

Route-6: Compounds of general formula (II) may be prepared by the following route,

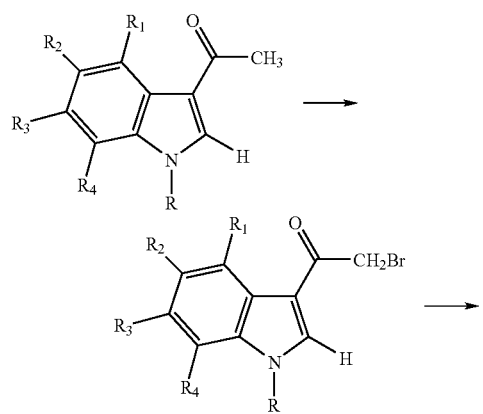

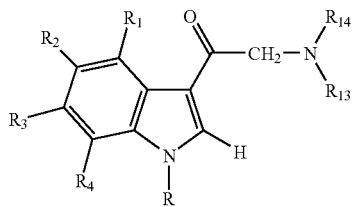

wherein $R_1, R_2, R_3, R_4, R_{11}, R_{12}, R_{13}, R_{14}$ and n are as defined in relation to formula (1); R represents either of hydrogen or a group such as,

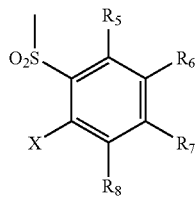

wherein X is halogen such as chloro, bromo or iodo; $R_5, R_6, R_7$ and $R_8$ are as defined earlier. The first step is bromination using suitable agent such as bromine, pyridinium-bromide and the like in a suiteble solvent. In the next step bromine is displaced by amine according to the methods known.

Route-7: Compounds of general formula (II) may be prepared by the following route,

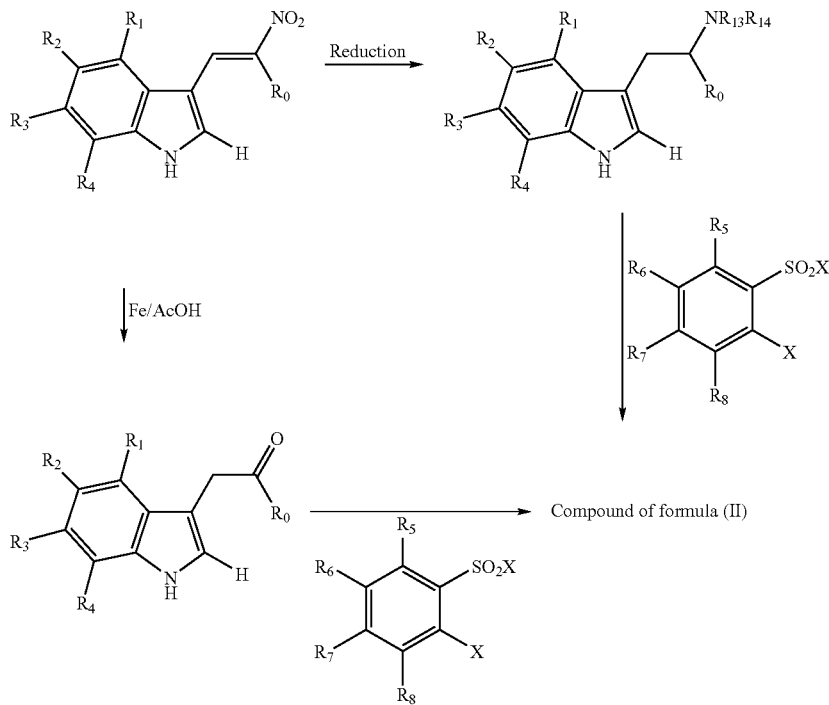

wherein $R_1$, $R_2$, $R_3$, $R_4$, $R_{11}$, $R_{12}$, $R_{13}$, $R_{14}$ and n (=2) are as defined in relation to formula (I); $R_0$ is hydrogen or alkyl group. The starting material is well-known intermediate in indole chemistry, which upon oxidization leads to $CH_2$—C (=O)— type substitution in the side chain. Next carrying out reaction sequence as described in Route 3 (i.e. reducing the carbonyl bond to hydroxyl) and Route 6 (i.e. bromination) differently substituted side chains can be prepared.

Novel intermediates of general formula (III) are represented as given below,

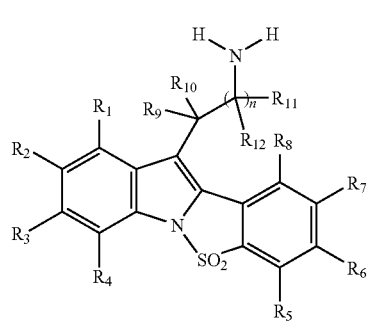

(III)

wherein $R_1$, $R_2$, $R_3$, $R_4$, $R_5$, $R_6$, $R_7$, $R_8$, $R_9$, $R_{10}$, $R_{11}$ and $R_{12}$ may be same or different and each independently represent hydrogen, halogen, oxo, thio, perhaloalkyl, hydroxy, amino, nitro, cyano, formyl, amidino, guanidino, substituted or unsubstituted groups such as linear or branched ($C_1$-$C_{12}$) alkyl, ($C_2$-$C_{12}$)alkenyl, ($C_2$-$C_{12}$)alkynyl, ($C_3$-$C_7$)cycloalkyl, ($C_3$-$C_7$)cycloalkenyl, bicycloalkyl, bicycloalkenyl, ($C_1$-$C_{12}$) alkoxy, cyclo($C_3$-$C_7$)alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_5$ and $R_6$ or $R_6$ and $R_7$ or $R_7$ and $R_8$ together with carbon atoms to which they are attached may form a 5, 6, or 7 membered ring, which may further optionally contain one or more double bonds and/or one or more heteroatoms such as the group "Oxygen", "Nitrogen", "Sulfur" or "Selenium" and combinations of double bond and heteroatoms; or $R_9$ and $R_{10}$ or $R_{11}$ and $R_{12}$ together represent double bond attached to "Oxygen" or "Sulfur"; or $R_9$ and $R_{10}$ or $R_{11}$ and $R_{12}$ together with the carbon atoms to which they are attached may form a 3, 4, 5, or 6 membered ring, which may further optionally contain one or more double bonds, and/or one or more heteroatoms such as the group "Oxygen", "Nitrogen", "Sulfur" or "Selenium" and also includes combination of one or more double bonds with "heteroatoms", as above defined.

"n" is an integer ranging from 1 to 8. It is preferred that n be 1 to 4. The carbon chains which "n" represents may be either linear or branched.

The present invention also provides a process for preparing the novel intermediate represented by the general formula (III).

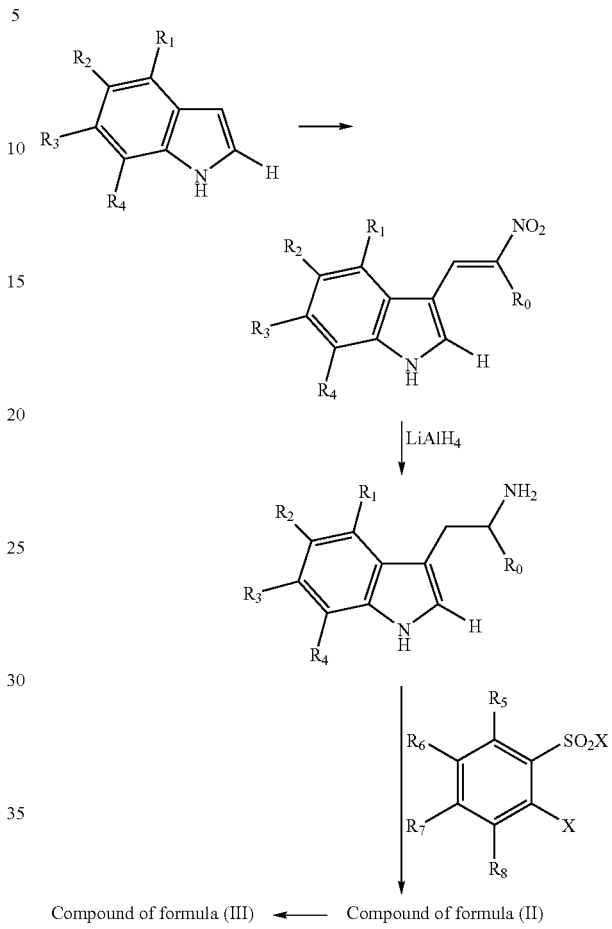

Compound of formula (III) ← Compound of formula (II)

Substituted indole compounds can be alkylated with 1-dimethylamino-2-nitroethylene in the presence of trifluoroacetic acid, which can reduced with lithium aluminium hydride to give substituted tryptamines. All steps are described in J. Med. Chem., 1993, 36, 4069 and J. Med Chem., 2000, 43,11011-1018.

The compounds of formula (II) can be methylated through reductive alkylation using formaldehyde, sodium cyanoborohydride in acetonitrile stirring at room temperature to produce compounds of formula (I).

Novel intermediates of general formula (IV) are represented as given below,

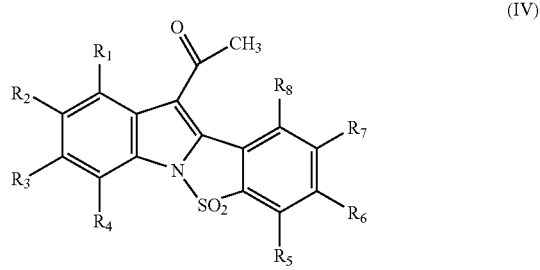

(IV)

wherein $R_1$, $R_2$, $R_3$, $R_4$, $R_5$, $R_6$, $R_7$ and $R_8$ are as may be same or different and each independently represent hydrogen, halogen, oxo, thio, perhaloalkyl, hydroxy, amino, nitro, cyano, formyl, amidino, guanidino, substituted or unsubstituted groups such as linear or branched ($C_1$-$C_{12}$)alkyl, ($C_2$-$C_{12}$) alkenyl, ($C_2$-$C_{12}$)alkynyl, ($C_3$-$C_7$)cycloalkyl, ($C_3$-$C_7$)cycloalkenyl, bicycloalkyl, bicycloalkenyl, ($C_1$-$C_{12}$)alkoxy, cyclo($C_6$-$C_7$)alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_5$ and $R_6$ or $R_6$ and $R_7$ or $R_7$ and $R_8$ together with carbon atoms to which they are attached may form a 5, 6, or 7 membered ring, which may further optionally contain one or more double bonds and/or one or more heteroatoms such as the group "Oxygen", "Nitrogen", "Sulfur" or "Selenium" and combinations of double bond and heteroatoms; and $R_9$ and $R_{10}$ here represent double bond attached to "Oxygen".

The present invention also provides method to prepare intermediate by general formula (IV), which comprises of cyclizing compounds of formula (VIII),

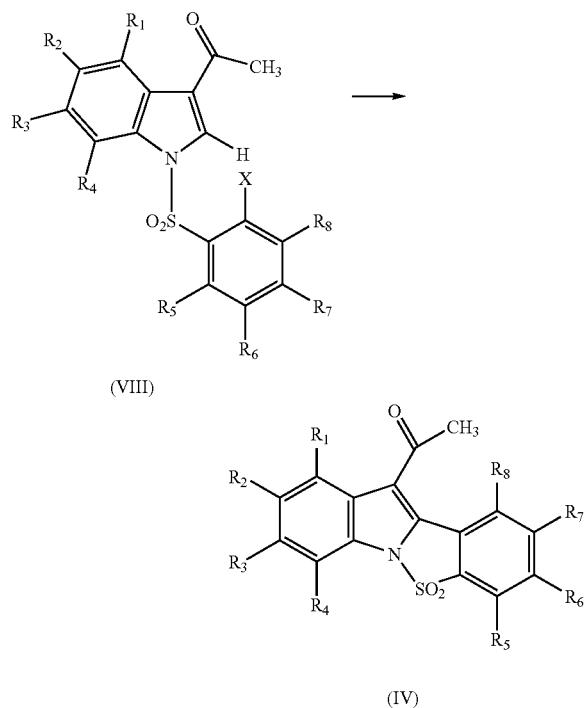

(VIII)

(IV)

wherein $R_1$, $R_2$, $R_3$, $R_4$, $R_5$, $R_6$, $R_7$ and $R_8$ are as defined above; using a Pd(0) or Pd (II) derivative as a catalyst, for example tetrakis triphenylphosphine palladium, (Bis-tri-o-tolylphosphine) palladium and the like in a suitable solvent.

During any of the above synthetic sequences it may be necessary and/or desirable to protect sensitive or reactive groups on any of the molecules concerned. This may be achieved by means of conventional protecting groups, such as those described in Protective Groups in Organic Chemistry, Ed J. F. W. McOmie, Plenum Press, 1973; and T. W. Greene & P. G. M. Wuts, Protective Groups in Organic Synthesis, John Wiley & Sons, 1991. For example, suitable protecting groups for the piperazine group include BOC, $COCCl_3$, $COCF_3$. The protecting groups may be removed according to the standard procedures.

The protecting groups may be removed at a convenient subsequent stage using methods known from the art.

The compounds of the present invention may contain one or more asymmetric centers and therefore they also exist as stereoisomers. The stereoisomers of the compounds of the present invention may be prepared by one or more ways presented below.

i) One or more of the reagents may be used in their optically active form.
ii) Optically pure catalyst or chiral ligands along with metal catalyst may be employed in the reduction process. The metal catalyst may be Rhodium, Ruthenium, Indium and the like. The chiral ligands may preferably be chiral phosphines (Principles of Asymmetric synthesis, J. E. Baldwin Ed., Tetrahedron series, 14, 311-316).
iii) The mixture of stereoisomers may be resolved by conventional methods such as forming a diastereomeric salts with chiral acids or chiral amines, or chiral amino alcohols, chiral amino acids. The resulting mixture of diastereomers may then be separated by methods such as fractional crystallization, chromatography and the like, which is followed by an additional step of isolating the optically active product by hydrolyzing the derivative (Jacques et. al., "Enantiomers, Racemates and Resolution", Wiley Interscience, 1981).
iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like.

The pharmaceutically acceptable salts forming a part of this invention may be prepared by treating the compound of formula (I) with 1-6 equivalents of a base such as Lithium, ammonia, substituted ammonia, sodium hydride, sodium methoxide, sodium ethoxide, sodium hydroxide, potassium t-butoxide, calcium hydroxide, calcium acetate, calcium chloride, magnesium hydroxide, magnesium chloride and the like. Solvents such as water, acetone, ether, THF, methanol, ethanol, t-butanol, dioxane, isopropanol, isopropyl ether or mixtures thereof may be used. Organic bases such lysine, arginine, methyl benzylamine, ethanolamine, diethanolamine, tromethamine, choline, guanidine and their derivatives may be used. Acid addition salts, wherever applicable may be prepared by treatment with acids such as tartaric acid, mandelic acid, fumaric acid, maleic acid, lactic acid, salicyclic acid, citric add, ascorbic acid, benzene sulfonic acid, p-toluene sulfonic acid, hydroxynaphthoic acid, methane sulfonic acid, malic acid, acetic acid, benzoic acid, succinic acid, palmitic acid, oxalic acid, hydrochloric acid, hydrobromic acid, sulfuric acid, nitric acid and the like in solvents such as water, alcohols, ethers, ethyl acetate, dioxane, DMF or a lower alkyl ketone such as acetone, or the mixtures thereof.

Different polymorphs may be prepared by crystallization of compounds of general formula (I) under different conditions such as different solvents or solvent mixtures in varying proportions for recrystallization, various ways of crystallization such as slow cooling, fast cooling or a very fast cooling or a gradual cooling during crystallization. Different polymorphs may also be obtained by heating the compound, melting the compound and solidification by gradual or fast cooling, heating or melting under vacuum or under inert atmosphere and cooling under either vacuum or inert atmosphere. The various polymorphs may be identified by either one or more of the following techniques such as differential scanning calorimeter, powder X-ray diffraction, IR spectroscopy, solid probe NMR spectroscopy and thermal microscopy.

Another aspect of the present invention comprises of a pharmaceutical composition, containing at least one of the compounds of the general formula (I), their derivatives, their analogs, their derivatives, their tautomeric forms, their stereoisomers, their geometric forms, their polymorphs, their pharmaceutically acceptable salts, their pharmaceutically acceptable solvates thereof as an active ingredient, together with pharmaceutically employed carriers, auxiliaries and the like.

The pharmaceutical compositions of the present invention may be formulated in a conventional manner using one or more pharmaceutically acceptable carriers. Thus, the active compounds of the invention may be formulated for oral, buccal, intranasal, parental (e.g., intravenous, intramuscular or subcutaneous) or rectal administration or a form suitable for administration by inhalation or insufflation.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer, or from a capsule using a inhaler or insufflator. In the case of a pressurized aerosol, a suitable propellant, e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule it preferably should be in the form of powder. Capsules and cartridges (made, for example, from gelatin) for use in an inhaler or insufflator may be formulated containing a powder mix of a compound of the invention and a suitable powder base such as lactose or starch.

A proposed dose of the active compounds of this invention, for either oral, parenteral, nasal or buccal administration, to an average adult human, for the treatment of the conditions referred to above, is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

The affinities of the compound of this invention for the various serotonin receptors are evaluated using standard radioligand binding assays and are described here.

Radioligand Binding Assays for Various 5-HT Receptor Sub-Types:

i) Assay for $5HT_{1A}$

Materials and Methods:

Receptor source: Human recombinant expressed in HEK-293 cells

Radioligand: [3H]-8-OH-DPAT (221 Ci/mmol)

Final ligand concentration—[0.5 nM]

Reference compound: 8-OH-DPAT

Positive control: 8-OH-DPAT

Incubation Conditions:

Reactions are carried out in 50 mM TRIS-HCl (pH 7.4) containing 10 mM $MgSO_4$, 0.5 mM EDTA and 0.1% Ascorbic acid at room temperature for 1 hour. The reaction is terminated by rapid vacuum filtration onto glass fiber filters. Radioactivity trapped onto the filters is determined and compared to control values in order to ascertain any interactions of test compound with the $5HT_{1A}$ binding site.

Literature Reference:
Hoyer D., Engel G., et al. Molecular Pharmacology of 5HT$_1$ and 5-HT$_2$ Recognition Sites in Rat and Pig Brain Membranes: Radioligand Binding Studies with [$^3$H]-5HT, [$^3$H]-8-OH-DPAT, [$^{125}$I]-Iodocyanopindolol, [$^3$H]-Mesulergine and [$^3$H]-Ketanserin. Eur. Jrnl. Pharmacol. 118: 13-23 (1985) with modifications.

Schoeffter P. and Hoyer D. How Selective is GR 43175? Interactions with Functional 5-HT$_{1A}$, 5HT$_{1B}$, 5-HT$_{1C}$, and 5-HT$_{1D}$ Receptors. Naunyn-Schmiedeberg's Arch. Pharmac. 340: 135-138 (1989) with modifications.

ii) Assay for 5HT$_{1B}$

Materials and Methods:
Receptor source: Rat striatal membranes
Radioligand: [$^{125}$I]Iodocyanopindolol (2200 Ci/mmol)
Final ligand concentration—[0.15 nM]
Non-specific determinant: Serotonin—[10 FM]
Reference compound: Serotonin
Positive control: Serotonin Incubation Conditions:
Reactions are carried out in 50 mM TRIS-HCl (pH 7.4) containing 60 FM (−) isoproterenol at 37° C. for 60 minutes. The reaction is terminated by rapid vacuum filtration onto glass fiber filters. Radioactivity trapped onto the filters is determined and compared to control values in order to ascertain any interactions of test compound with the 5HT$_{1B}$ binding site.

Literature Reference:
Hoyer D., Engel G., et al. Molecular Pharmacology of 5HT$_1$ and 5-HT$_2$ Recognition Sites in Rat and Pig Brain Membranes: Radioligand Binding Studies with [$^3$H]-5HT, [$^3$H]-8-OH-DPAT, [$^{125}$I]-Iodocyanopindolol, [$^3$H]-Mesulergine and [$^3$H]-Ketanserin. *Eur. Jrnl. Pharmacol.* 118: 13-23 (1985) with modifications.

Schoeffter P. and Hoyer D. How selective is GR 43175? Interactions with Functional 5HT$_{1A}$, 5HT$_{1B}$, 5-HT$_{1C}$, and 5-HT$_{1D}$ Receptors. *Naunyn-Schmiedeberg's Arch. Pharmac.* 340: 135-138 (1989) with modifications.

iii) Assay for 5HT$_{1D}$

Materials and Methods:
Receptor source: Human cortex
Radioligand: [$^3$H] 5-Carboxamidotryptamine (20-70 Ci/mmol)
Final ligand concentration-[2.0 nM]
Non-specific determinant: 5-Carboxamidotryptamine (5-CT) -[1.0 µM]
Reference compound: 5-Carboxamidotryptamine (5-CT)
Positive control: 5-Carboxamidotryptamine (5-CT)

Incubation Conditions:
Reactions are carried out in 50 mM TRIS-HCl (pH 7.7) containing 4 mM CaCl$_2$, 100 nM 8-OH-DPAT, 100 nM Mesulergine, 10 uM Pargyline and 0.1% ascorbic acid at 25° C. for 60 minutes. The reaction is terminated by rapid vacuum filtration onto glass fiber filters. Radioactivity trapped onto the filters is determined and compared to control values in order to ascertain any interactions of test compound with the cloned 5HT$_{1D}$ binding site.

Literature Reference:
Waeber C., Schoeffter, Palacios J. M. and Hoyer D. Molecular Pharmacology of the 5-HT$_{1D}$ Recognition Sites: Radioligand Binding Studies in Human, Pig, and Calf Brain Membranes. Naunyn-Schmiedeberg's Arch. Pharmacol. 337: 595-601 (1988) with modifications.

iv) Assay for 5HT$_{2A}$

Materials and Methods:
Receptor source: Human Cortex
Radioligand: [$^3$H] Ketanserin (6090 Ci/mmol)
Final ligand concentration—[2.0 nM]
Non-specific determinant: Ketanserin—[3.0 µM]
Reference compound: Ketanserin
Positive control: Ketanserin Incubation Conditions:
Reactions are carried out in 50 mM TRIS-HCl (pH 7.5) at room temperature for 90 minutes. The reaction is terminated by rapid vacuum filtration onto glass fiber filters. Radioactivity trapped onto the filters is determined and compared to control values in order to ascertain any interactions of test compound with the 5HT$_{2A}$ binding site.

Literature Reference:
Leysen J. E., Niemegeers C. J., Van Nueten J. M. and Laduron P. M. [$^3$H]Ketanserin: A Selective Tritiated Ligand for Serotonin$_2$ Receptor Binding Sites. Mol. Pharmacol. 21: 301-314 (1982) with modifications.

Martin, G. R. and Humphrey, P. P. A. Classification Review. Receptors for 5-HT: Current Perspectives on Classification and Nomenclature. Neuropharmacol. 33(3/4): 261-273 (1994).

Assay for 5HT$_{2C}$

Materials and Methods:
Receptor source: Pig choroid plexus membranes
Radioligand: [$^3$H] Mesulergine (50-60 Ci/mmol)
Final ligand concentration—[1.0 nM]
Non-specific determinant: Serotonin—[100 µM]
Reference compound: Mianserin
Positive control: Mianserin Incubation Conditions:
Reactions are carried out in 50 mM TRIS-HCl (pH 7.7) containing 4 mM CaCl$_2$ and 0.1% ascorbic acid at 37° C. for 60 minutes. The reaction is terminated by rapid vacuum filtration onto glass fiber filters. Radioactivity trapped onto the filters is determined and compared to control values in order to ascertain any interactions of test compound with the 5HT$_2$C binding site.

Literature Reference:
A. Pazos, D. Hoyer, and J. Palacios. The Binding of Serotonergic Ligands to the Porcine Choroid Plexus: Characterization of a New Type of Serotonin Recognition Site. Eur. Jrnl. Pharmacol. 106: 539-546 (1985) with modifications.

Hoyer, D., Engel, G., et al. Molecular Pharmacology of 5HT$_1$ and 5-HT$_2$ Recognition Sites in Rat and Pig Brain Membranes: Radioligand Binding Studies with [3H]-5HT, [3H]-8-OH-DPAT, [$^{125}$I]-Iodocyanopindolol, [3H]Mesulergine and [3H]-Ketanserin. Eur. Jrnl. Pharmacol. 118: 13-23 (1985) with modifications.

v) Assay for 5HT$_3$

Materials and Methods:
Receptor source: N 1 E-115 cells
Radioligand :[$^3$H]-GR 65630 (30-70 Ci/mmol)
Final ligand concentration—[0.35 nM]
Non-specific determinant: MDL-72222-[1.0 ELM]
Reference compound: MDL-72222
Positive control: MDL-72222

Incubation Conditions:

Reactions are carried out in 20 mM HEPES (pH 7.4) containing 150 mM NaCl at 25° C. for 60 minutes. The reaction is terminated by rapid vacuum filtration onto glass fiber filters. Radioactivity trapped onto the filters is determined and compared to control values in order to ascertain any interactions of test compound with the $5HT_3$ binding site.

Literature Reference:
- Lummis S. C. R., Kilpatrick G. J. Characterization of $5HT_3$ Receptors in Intact NIE-115 Neuroblastoma Cells. Eur. Jrnl. Pharmacol. 189: 223-227 (1990) with modifications.
- Hoyer D. and Neijt H. C. Identification of Serotonin $5-HT_3$ Recognition Sites in Membranes of N1E-115 Neuroblastoma Cells by Radioligand Binding. Mol. Pharmacol. 33: 303 (1988).
- Tyers M. B. $5-HT_3$ Receptors and the Therapeutic Potential of $5HT_3$ Receptor Antagonists. Therapie. 46:431-435 (1991).

vi) Assay for $5HT_4$

Materials and Methods:
Receptor source: Guinea pig striatal membranes
Radioligand: [$^3$H] GR-113808 (30-70 Ci/mmol)
Final ligand concentration—[0.2 nM]
Non-specific determinant: Serotonin (5-HT)—[30 µM]
Reference compound: Serotonin (5-HT)
Positive control: Serotonin (5-HT)

Incubation Conditions:

Reactions are carried out in 50 mM HEPES (pH 7.4) at 370 C for 60 minutes. The reaction is terminated by rapid vacuum filtration onto glass fiber filters. Radioactivity trapped onto the filters is determined and compared to control values in order to ascertain any interactions of test compound with the $5HT_4$ binding site.

Literature Reference:
- Grossman Kilpatrick, C., et al. Development of a Radioligand Binding Assay for $5HT_4$ Receptors in Guinea Pig and Rat Brain. Brit. J Pharmco. 109: 618-624 (1993).

vii) Assay for $5HT_{5A}$

Materials and Methods:
Receptor source: Human recombinant expressed in HEK 293 cells
Radioligand: [$^3$H] LSD (60-87 Ci/mmol)
Final ligand concentration—[1.0 nM]
Non-specific determinant: Methiothepin mesylate—[1.0 µM]
Reference compound: Methiothepin mesylate
Positive control: Methiothepin mesylate Incubation Conditions:

Reactions are carried out in 50 mM TRIS-HCl (pH 7.4) containing 10 mM $MgSO_4$ and 0.5 mM EDTA at 37° C. for 60 minutes. The reaction is terminated by rapid vacuum filtration onto glass fiber filters. Radioactivity trapped onto the filters is determined and compared to control values in order to ascertain any interactions of test compound with the cloned $5HT_{5A}$ binding site.

Literature Reference:
- Rees S., et al. FEBS Letters, 355: 242-246 (1994) with modifications viii) Assay for $5HT_6$ Materials and Methods:
Receptor source: Human recombinant expressed in HEK293 cells
Radioligand: [$^3$H]LSD (60-80 Ci/mmol)
Final ligand concentration—[1.5 nM]
Non-specific determinant: Methiothepin mesylate—[0.1 µM]
Reference compound: Methiothepin mesylate
Positive control: Methiothepin mesylate Incubation Conditions:

Reactions are carried out in 50 mM TRIS-HCl (pH 7.4) containing 10 mM $MgCl_2$, 0.5 mM EDTA for 60 minutes at 37° C. The reaction is terminated by rapid vacuum filtration onto glass fiber filters. Radioactivity trapped onto the filters is determined and compared to control values in order to ascertain any interactions of test compound(s) with the cloned serotonin—$5HT_6$ binding site.

Literature Reference:
- Monsma F. J. Jr., et al., Molecular Cloning and Expression of Novel Serotonin Receptor with High Affinity for Tricyclic Psychotropic Drugs. Mol. Pharmacol. (43): 320-327 (1993).

ix) Assay for $5-HT_7$

Materials and Methods:
Receptor source: Human recombinant expressed in CHO cells
Radioligand: [$^3$H]LSD (60-80 Ci/mmol)
Final ligand concentration—[2.5 nM]
Non-specific determinant: 5-Carboxamidotryptamine (5CT) -[0.1 µM]
Reference compound: 5-Carboxamidotryptamine
Positive control: 5-Carboxamidotryptamine Incubation Conditions:

Reactions are carried but in 50 mM TRIS-HCl (pH 7.4) containing 10 mM $MgCl_2$, 0.5 mM EDTA for 60 minutes at 37° C. The reaction is terminated by rapid vacuum filtration onto glass fiber filters. Radioactivity trapped onto the filters is determined and compared to control values in order to ascertain any interactions of test compound(s) with the cloned serotonin—$5HT_7$ binding site.

Literature Reference:
- Y. Shen, E. Monsma, M. Metcalf, P. Jose, M Hamblin, D. Sibley, Molecular Cloning and Expression of a 5-hydroxytryptamine7 Serotonin Receptor Subtype. J. Biol. Chem. 268: 18200-18204.

The following description illustrates the method of preparation of variously substituted compounds of general formula (I), according to the methods described herein. These are provided by the way of illustration only and therefore should not be construed to limit the scope of the invention.

Commercial reagents were utilized without further purification. Room temperature refers to 25-30° C. Melting points are uncorrected. IR spectra were taken using KBr and in solid state. Unless otherwise stated, all mass spectra were carried out using ESI conditions. 1H NMR spectra were recorded at 300 MHz on a Bruker instrument Deuterated chloroform (99.8% D) was used as solvent. TMS was used as internal reference standard. Chemical shift values are expressed in are reported in parts per million (δ)-values. The following abbreviations are used for the multiplicity for the NMR signals: s=singlet, bs=broad singlet, d=doublet, t-triplet, q=quartet, qui=quintet, h=heptet, dd=double doublet, dt=double triplet, tt=triplet of triplets, m=multiplet. NMR, mass were corrected for background peaks. Specific rotations were measured at room temperature using the sodium D (589 nm). Chromatography refers to column chromatography performed using 60-120 mesh silica gel and executed under nitrogen pressure (flash chromatography) conditions.

Description 1: N,N-Dimethyl-1-(2'-bromophenylsulfonyl)tryptamine (D1)

A suspension of potassium hydride (9.0 mmoles, 1.2 g. (30% suspension in mineral oil), washed with THF before use), in THF was stirred and cooled at 0-5° C. To this cooled solution was added a solution of N,N-dimethyltryptamine (6.0 mmoles), in THF, slowly, over 15 min., maintaining the temperature below 10° C. After completion of addition, the mixture was warmed to 25-30° C. and maintained for 30-45 min. The reaction mixture was then cooled to 0-5° C. and solution of 2-bromobenzenesulfonyl chloride in THF (6.0 mmoles, 1.7 g. in 7 mL of THF) was then added to the above well stirred mixture, maintaining the reaction temperature below 10° C. (Exothermic reaction). The reaction mixture was maintained at 20-25° C. for further 2-4 hrs. After completion of reaction (TLC), the excess of THF was distilled off and the concentrate was diluted with ice-water and extracted with ethyl acetate. Combined ethyl acetate layer was washed with water, dried over sodium sulfate and evaporated under reduced pressure, below 50° C.

The crude residue was purified by silica gel column chromatography using 30% methanol in ethyl acetate as a mobile phase, to obtain the intermediate, N,N-Dimethyl-1-(2'-bromophenylsulfonyl)tryptamine, which was identified by IR, NMR and mass spectral analyses.

Description 2-55 (D2- D55):

Various indole intermediates were subjected to aryl sulfonylation using substituted 2-bromobenzenesulfonyl chloride according to the procedure described in the description 1. These compounds were identified by IR, NMR and mass spectral analyses. The following list includes list of such compounds.

List-1

| | Description | Mass ion $(M + H)^+$ |
|---|---|---|
| D1 | 2-[1-(2-Bromophenylsulfonyl)indol3-yl]ethyl-N,N-dimethylamine | 407 |
| D2 | 2-[1-(2-Bromophenylsulfonyl)-5-bromoindol3-yl]ethyl-N,N-dimethylamine | 485 |
| D3 | 2-[1-(2-Bromophenylsulfonyl)-5-chloroindol3-yl]ethyl-N,N-dimethylamine | 441 |
| D4 | 2-[1-(2-Bromophenylsulfonyl)-5-fluoroindol3-yl]ethyl-N,N-dimethylamine | 425 |
| D5 | 2-[1-(2-Bromophenylsulfonyl)-5-methylindol3-yl]ethyl-N,N-dimethylamine | 421 |
| D6 | 2-[1-(2-Bromophenylsulfonyl)-5-methoxyindol3-yl]ethyl-N,N-dimethylamine | 437 |
| D7 | 2-[1-(2-Bromo-4-methoxyphenylsulfonyl)indol3-yl]ethyl-N,N-dimethylamine | 437 |
| D8 | 2-[1-(2-Bromo-4-methoxyphenylsulfonyl)-5-bromoindol3-yl]ethyl-N,N-dimethylamine | 515 |
| D9 | 2-[1-(2-Bromo-4-methoxyphenylsulfonyl)-5-chloroindol3-yl]ethyl-N,N-dimethylamine | 471 |
| D10 | 2-[1-(2-Bromo-4-methoxyphenylsulfonyl)-5-fluoroindol3-yl]ethyl-N,N-dimethylamine | 455 |
| D11 | 2-[1-(2-Bromo-4-methoxyphenylsulfonyl)-5-methylindol3-yl]ethyl-N,N-dimethylamine | 451 |
| D12 | 2-[1-(2-Bromo-4-methoxyphenylsulfonyl)-5-methoxyindol3-yl]ethyl-N,N dimethylamine | 467 |
| D13 | 2-[1-(2-Bromophenylsulfonyl)-7-ethylindol3-yl]ethyl-N,N-dimethylamine | 435 |
| D14 | 2-[1-(2-Bromophenylsulfonyl)-7-chloroindol3-yl]ethyl-N,N-dimethylamine | 441 |
| D15 | 2-[1-(2-Bromophenylsulfonyl)-5,7-dichloroindol3-yl]ethyl-N,N-dimethylamine | 475 |
| D16 | 2-[1-(2-Bromophenylsulfonyl)-6,7-dichloroindol3-yl]ethyl-N,N-dimethylamine | 475 |
| D17 | 2-[1-(2-Bromophenylsulfonyl)-4-chloro-7-methylindol3-yl]ethyl-N,N-dimethylamine | 455 |
| D18 | 2-[1-(2-Bromophenylsulfonyl)-4-chloro-7-methoxyindol3-yl]ethyl-N,N-dimethylamine | 471 |
| D19 | 2-[1-(2-Bromophenylsulfonyl)-4,6,7-trichloro-indol3-yl]ethyl-N,N-dimethylamine | 509 |
| D20 | 2-[1-(2-Bromophenylsulfonyl)-5,7-difluoroindol3-yl]ethyl-N,N-dimethylamine | 443 |
| D21 | 2-[1-(2-Bromo-4-methylphenylsulfonyl)-5,7-difluoroindol3-yl]ethyl-N,N-dimethylamine | 457 |
| D22 | 2-[1-(2-Bromo-4-methylphenylsulfonyl)-5-fluoroindol3-yl]ethyl-N,N-dimethylamine | 439 |
| D23 | 2-[1-(2-Bromophenylsulfonyl)-7-methoxyindol3-yl]ethyl-N,N-dimethylamine | 421 |
| D24 | 2-[1-(2-Bromo-4-methoxyphenylsulfonyl)-7-methoxyindol3-yl]ethyl-N,N-dimethylamine | 467 |
| D25 | 2-[1-(2-Bromo-4-methylphenylsulfonyl)indol3-yl]ethyl-N,N-dimethylamine | 421 |
| D26 | 1-[1-(2-Bromobenzenesulfonyl)-5-bromo-1H-indol-3-yl]-3-dimethylamino-propan-1-ol | 515 |
| D27 | 1-[1-(2-Bromo-4-methoxybenzenesulfonyl)-1H-indol-3-yl]-3-dimethylamino-propan-1-ol | 467 |
| D28 | 1-[1-(2-Bromo-4-methylbenzenesulfonyl)-1H-indol-3-yl]-3-dimethylamino-propan-1-ol | 451 |

-continued

| | Description | Mass ion (M + H)+ |
|---|---|---|
| D29 | 1-[1-(2-Bromo-4-methoxybenzenesulfonyl)-5-bromo-1H-indol-3-yl]-3-dimethylamino-propan-1-ol | 545 |
| D30 | 1-(2-Bromobenzenesulfonyl)-3-[2-(4-methyl-piperazin-1-yl)ethyl]-1H-indole | 462 |
| D31 | 1-(2-Bromobenzenesulfonyl)-3-[2-(morpholin-1-yl)ethyl]-1H-indole | 449 |
| D32 | 1-(2-Bromobenzenesulfonyl)-3-[2-(pyrrolidin-1-yl)ethyl]-1H-indole | 433 |
| D33 | 1-(2-Bromobenzenesulfonyl)-3-[2-(piperidin-1-yl)ethyl]-1H-indole | 447 |
| D34 | 1-(2-Bromobenzenesulfonyl)-5-bromo-3-[2-(4-methyl-piperazin-1-yl)ethyl]-1H-indole | 540 |
| D35 | 1-(2-Bromobenzenesulfonyl)-5-bromo-3-[2-(morpholin-1-yl)ethyl]-1H-indole | 527 |
| D36 | 1-(2-Bromobenzenesulfonyl)-5-bromo-3-[2-(pyrrolidin-1-yl)ethyl]-1H-indole | 511 |
| D37 | 1-[1-(2-Bromobenzenesulfonyl)-1H-indol-3-yl]-3-(piperidin-1-yl)-propan-1-ol | 477 |
| D38 | 1-[1-(2-Bromo-4-methoxybenzenesulfonyl)-1H-indol-3-yl]-3-(piperidin-1-yl)-propan-1-ol | 507 |
| D39 | 1-[1-(2-Bromobenzenesulfonyl)-5-bromo-1H-indol-3-yl]-3-(piperidin-1-yl)-propan-1-ol | 555 |
| D40 | 1-[1-(2-Bromo-4-methoxybenzenesulfonyl)-5-bromo-1H-indol-3-yl]-3-(piperidin-1-yl)-propan-1-ol | 587 |
| D41 | 1-[1-(2-Bromobenzenesulfonyl)-1H-indol-3-yl]-3-(pyrrolidin-1-yl)-propan-1-ol | 463 |
| D42 | 1-[1-(2-Bromo-4-methoxybenzenesulfonyl)-1H-indol-3-yl]-3-(pyrrolidin-1-yl)-propan-1-ol | 493 |
| D43 | {2-[1-(2-Bromobenzenesulfonyl)-1H-indol-3-yl]-1-methylethyl}-N,N-dimethylamine | 421 |
| D44 | 1-[1-(2-Bromo-benzenesulfonyl)-1H-indol-3-yl]-2-dimethylamino-propan-1-ol | 437 |

Description 45: 2-(Benzo[d]isothiazolo[3,2-a]-1H-indol-3-yl-S,S-dioxide)ethylamine (D45)

2-[1-(2-Bromobenzenesulfonyl)-1H-indol-3-yl]ethylamine (0.286 mmoles) was taken in a 100 mL 3 necked round bottomed flask, along with N,N-dimethyl acetamide (40 mL), potassium acetate (0.343 mmoles, 0.337 g.) and dichloro bis(tri-o-tolylphosphine)palladium (0.0143 mmoles, 0.0112 g.). The reaction mixture was maintained under nitrogen atmosphere and was heated to 140 to 160° C. with stirring for 2 to 5 hrs. After the completion of reaction (TLC), the reaction mass is filtered over hyflow, washed with ethyl acetate, and the combined filtrate was diluted with cold water. The aqueous layer was extracted with ethyl acetate (3×50 mL). Combined ethyl acetate layer was washed with brine, dried over sodium sulfate and evaporated under reduced pressure, below 50° C.

The residue obtained was purified by silica gel column chromatography using 20% methanol in ethyl acetate as an eluent, to afford the title compound, which was identified by IR, NMR and mass spectral analyses.

Mass (m/z): 299 (M+H)+

EXAMPLE-1

6-(2-N,N-Dimethylaminoethyl)benzo[d]isothiazolo[3,2-a]indol-S,S-dioxide 1-(2'-bromophenylsulfonyl)-N,N-dimethyltryptamine (0.286 moles) was taken in a 100 mL 3 necked round bottomed flask, along with N,N-dimethyl acetamide (40 mL), potassium acetate (0.286 moles, 0.281 g.) and dichloro bis(tri-o-tolylphosphine)palladium (0.0143 moles, 0.0126 g.). The reaction mixture was maintained under nitrogen atmosphere and was heated to 160° C. with stirring for 16 hrs. After the completion of reaction (TLC), excess of dimethyl acetamide was distilled off under reduced pressure.

The residue obtained was purified by silica gel column chromatography using 20% methanol in ethyl acetate as an eluent, to afford the title compound, which was identified by IR, NMR and mass spectral analyses. The final desired compound of general formula (I) can be further purified by preparation of their acid addition salts. Melting range (° C.): 128-131; IR spectra (cm$^{-1}$): 2946, 1601, 1461, 1443; Mass (m/z): 327 (M+H)+; $^1$H-NMR (δ, ppm) 2.39 (6H, s), 2.58-2.66 (2H, m), 3.11-3.19 (2H, m), 7.22-7.86 (8H, m).

EXAMPLE-2

4-Bromo-6-(2-N,N-dimethylaminoethyl)benzo[d]isothiazolo[3,2-a]indol-S,S-dioxide

Using essentially the general procedure described in example 1 and some non-critical variations, the above derivative was prepared. Melting range (° C.): 162-165; IR spectra (cm$^{-1}$): 2969, 2770, 1344, 1176; Mass (m/z): 405 (M+H)+, 407 (M+3)+; $^1$H-NMR (δ ppm): 2.40 (6H, s), 2.58-2.66 (2H, m), 3.08-3.16 (2H, m), 7.46-7.89 (7H, m).

EXAMPLE-3

4-Chloro-6-(2-N,N-dimethylaminoethyl)-benzo[d]isothiazolo[3,2-a]indol-S,S-dioxide Using essentially the general procedure described in example 1 and some non-critical variations, the above derivative was prepared. Melting range (° C.): 156-158; IR spectra (cm$^{-1}$): 2941, 2768, 1440, 1344; Mass (m/z): 361 (M+H)+; $^1$H-NMR (δ ppm): 2.51 (6H, s), 2.72-2.80 (2H, m), 3.16-3.25 (2H, m), 7.32-7.95 (7H, m).

EXAMPLE-4

6-(2-N,N-Dimethylaminoethyl)-4-fluorobenzo[d]
isothiazolo[3,2-a]indol-S,S-dioxide Using essentially the general procedure described in example 1 and some non-critical variations, the above derivative was prepared. Melting range (° C.): 136-140; IR spectra (cm$^{-1}$): 2966, 1463, 1327; Mass (m/z): 345 (M+H)$^+$; $^1$H-NMR (δ ppm): 2.38 (6H, s), 2.55-2.64 (2H, s), 3.05-3.14 (2H, m), 7.06-7.86 (7H, m).

EXAMPLE-5

6-(2-N,N-Dimethylaminoethyl)-4-methylbenzo[d]
isothiazolo[3,2-a]indol-S,S-dioxide Using essentially the general procedure described in example 1 and some non-critical variations, the above derivative was prepared. Melting range (° C.): 138-142; IR spectra (cm$^{-1}$): 2941, 1607, 1332, 1177; Mass (m/z): 341 (M+H)$^+$; $^1$H-NMR (δ ppm): 2.40 (6H, s), 2.45 (3H, s), 2.58-2.66 (2H, s), 3.08-3.16 (2H, m), 7.20-7.80 (7H, m).

EXAMPLE-6

6-(2-N,N-Dimethylaminoethyl)-4-methylbenzo[d]
isothiazolo[3,2-a]indol-S,S-dioxide hydrochloride
salt Example no. 5 (19.8 mg) was dissolved in 3 mL ether. To this dear solution a mixture of isopropylalcohol-hydrochloric acid (1 mL) was added. Immediately a white precipitate separates out, which was filtered, washed with ether and dried. Melting range (° C.): >250 (dec).

EXAMPLE-7

6-(2-N,N-Dimethylaminoethyl)-4-methylbenzo[d]
isothiazolo[3,2-a]indol-S,S-dioxide maleic acid salt Example no. 5 (19.4 mg) was dissolved in 3 mL ether. To this clear solution a solution of maleic acid (7.3 mg, dissolved in 3 mL ether 0.5 mL methanol) was added. Immediately a white precipitate separates out, which was filtered, washed with ether and dried. Melting range (° C.): 192-194 (dec).

EXAMPLE-8

6-(2-N,N-Dimethylaminoethyl)-4-methylbenzo[d]
isothiazolo[3,2-a]indol-S,S-dioxide D,L-malic acid
salt Example no. 5 (19.8 mg) was dissolved in 3 mL ether. To this clear solution a solution of D,L-malic acid (8.4 mg, dissolved in 3 mL ether:0.5 mL methanol) was added. Immediately a white precipitate separates out, which was filtered, washed with ether and dried. Melting range (° C.): 202-204 (dec).

EXAMPLE-9

6-(2-N,N-Dimethylaminoethyl)-4-methylbenzo[d]
isothiazolo[3,2a]indol-S,S-dioxide oxalate salt Example no. 5 (19.7 mg) was dissolved in 3 mL ether. To this clear solution a solution of oxalic acid (8.1 mg, dissolved in 3 mL ether:0.5 mL methanol) was added. Immediately a white precipitate separates out, which was filtered, washed with ether and dried. Melting range (° C.): 226-228 (dec).

EXAMPLE-10

6-(2-N,N-Dimethylaminoethyl)-4-methylbenzo[d]
isothiazolo[3,2-a]indol-S,S-dioxide citrate salt Example no. 5 (20.2 mg) was dissolved in 3 mL ether. To this clear solution a solution of citric acid (12.0 mg, dissolved in 3 mL ether:0.5 mL methanol) was added. Immediately a white precipitate separates out, which was filtered, washed with ether and dried. Melting range (° C.): 184-186 (dec).

EXAMPLE-11

6-(2-N,N-Dimethylaminoethyl)-4-methoxybenzo[d]
isothiazolo[3,2-a]indol-S,S-dioxide Using essentially the general procedure described in example 1 and some non-critical variations, the above derivative was prepared. Melting range (° C.): 148-150; IR spectra (cm$^{-1}$): 2936, 1613, 1463, 1327; Mass (m/z): 357 (M+H)$^+$; $^1$H-NMR (δ ppm): 2.39 (6H, s), 2.56-2.64 (2H, m), 3.06-3.14 (2H, m), 3.86 (3H, s), 6.98-7.84 (7H, m).

EXAMPLE-12

6-(2-N,N-Dimethylaminoethyl)-8-methoxybenzo[d]
isothiazolo[3,2-a]indol-S,S-dioxide Using essentially the general procedure described in example 1 and some non-critical variations, the above derivative was prepared. Melting range (° C.): 146-150; IR spectra (cm$^{-1}$): 2933, 1603, 1438, 1325; Mass (m/z): 357 (M+H)$^+$; $^1$H-NMR (δ ppm): 2.40 (6H, s), 2.58-2.66 (2H, m), 3.09-3.18 (2H, m), 3.94 (3H, s), 6.93-7.77 (7H, m).

EXAMPLE-13

4-Bromo-6-(2-N,N-dimethylaminoethyl)-8-methoxybenzo[d]isothiazolo[3,2-a]indol-S,S-dioxide Using essentially the general procedure described in example 1 and some non-critical variations, the above derivative was prepared. Melting range (° C.):158-160; IR spectra (cm$^{-1}$): 2964, 2759, 1434, 1174; Mass (m/z): 435 (M+H)$^+$, 437 (M+3)$^+$; $^1$H-NMR (δ ppm): 2.40 (6H, s), 2.57-2.65 (2H, m), 3.05-3.13 (2H, m), 3.94 (3H, s), 6.96-7.78 (6H, m).

EXAMPLE-14

4-Chloro-6-(2-N,N-dimethylaminoethyl)-8-methoxybenzo[d]isothiazolo[3,2-a]indol-S,S-dioxide Using essentially the general procedure described in example 1 and some non-critical variations, the above derivative was prepared. Melting range (° C.): 172-174; IR spectra (cm-1): 2970, 2762, 1590, 1324; Mass (m/z): 391 (M+H)$^+$; $^1$H-NMR (δ ppm) 2.39 (6H, s), 2.56-2.65 (2H, m), 3.09-3.13 (2H, m), 3.94 (3H, s), 6.96-7.78 (6H, m).

EXAMPLE-15

6-(2-N,N-Dimethylaminoethyl)-4-fluoro-8-methoxy-benzo[d]isothiazolo[3,2-a]indol-S,S-dioxide Using essentially the general procedure described in example 1 and some non-critical variations, the above derivative was prepared. Melting range (° C.): 148-156; IR spectra (cm$^{-1}$): 2943, 1600, 1472, 1438; Mass (m/z): 375 (M+H)$^+$; $^1$H-NMR (δ ppm): 2.38 (6H, s), 2.56-2.64 (2H, m), 3.00-3.12 (2H, m), 3.94 (3H, s), 6.95-7.77 (6H, m).

EXAMPLE-16

6-(2-N,N-Dimethylaminoethyl)-4methyl-8-methoxy-benzo[d]isothiazolo[3,2-a]indol-S,S-dioxide Using essentially the general procedure described in example 1 and some non-critical variations, the above derivative was prepared. Melting range (° C.): 126-130; IR spectra (cm$^{-1}$): 2963, 1590, 1324, 1174; Mass (m/z): 371 (M+H)$^+$; $^1$H-NMR (δ ppm): 2.40 (6H, s), 2.46 (3H, s), 2.57-2.66 (2H, s), 3.11-3.15 (2H, m), 3.94 (3H, s), 6.92-7.60 (6H, m).

EXAMPLE-17

6-(2-N,N-Dimethylaminoethyl)-4,8-dimethoxybenzo[d]isothiazolo[3,2-a]indol-S,S-dioxide Using essentially the general procedure described in example 1 and some non-critical variations, the above derivative was prepared. Melting range (δ C.): 160-164; IR spectra (cm$^{-1}$): 2963, 2760, 1591, 1478, 1321, 1171; Mass (m/z): 387 (M+H)$^+$; $^1$H-NMR (δ ppm): 2.40 (6H, s), 2.57-2.65 (2H, m), 3.05-3.14 (2H, m), 3.87 (3H, s), 6.90-7.75 (6H, m).

EXAMPLE-18

6-(2-N,N-Dimethylaminoethyl)-2-ethylbenzo[d]isothiazolo[3,2-a]indol-S,S-dioxide Using essentially the general procedure described in example 1 and some non-critical variations, the above derivative was prepared. Mass (m/z): 319 (M+H)$^+$;

EXAMPLE-19

2-Chloro-6-(2-N,N-dimethylaminoethyl)benzo[d]isothiazolo[3,2-a]indol-S,S-dioxide Using essentially the general procedure described in example 1 and some non-critical variations, the above derivative was prepared. Melting range (° C.): 166-170; IR spectra (cm$^{-1}$): 2966, 2770, 1440, 1345; Mass (m/z): 361 (M+H)$^+$; $^1$H-NMR (δ, ppm) 2.38 (6H, s), 2.55-2.62 (2H, m), 3.10-3.19 (2H, m), 7.16-7.89 (7H, m).

EXAMPLE-20

2,4-Dichloro-6-(2-N,N-dimethylaminoethyl)-benzo[d]isothiazolo[3,2-a]indol-S,S-dioxide Using essentially the general procedure described in example 1 and some non-critical variations, the above derivative was prepared. Melting range (° C.): 112-116; IR spectra (cm$^{-1}$): 2964, 1614, 1559, 1342; 1179, 823, 796; Mass (m/z): 395 (M+H)$^+$; $^1$H-NMR (δ ppm): 2.42 (6H, s), 2.63-2.67 (2H, m), 3.10-3.18 (2H, m), 7.34-7.89 (6H, m).

EXAMPLE-21

5-Chloro-6-(2-N,N-dimethylaminoethyl)-2-methyl-benzo[d]isothiazolo[3,2-a]indol-S,S-dioxide Using essentially the general procedure described in example 1 and some non-critical variations, the above derivative was prepared. Melting range (° C.): 153-154; Mass (m/z): 375 (M+H)$^+$; $^1$H-NMR (δ ppm): 2.42 (6H, s), 2.65-2.73 (2H, m), 2.79 (3H, s), 3.42-3.51 (2H, m), 7.02-7.93 (6H, m).

EXAMPLE-22

2,4,5-Trichloro-6-(2-N,N-dimethylaminoethyl)-benzo[d]isothiazolo[3,2-a]indol-S,S-dioxide Using essentially the general procedure described in example 1 and some non-critical variations, the above derivative was prepared. Mass (m/z): 447 (M+18)$^+$, 449 (M+18)$^+$; $^1$H-NMR (δ ppm): 2.37 (6H, s), 2.67-2.75 (2H, m), 3.09-3.17 (2H, m), 7.15-8.05 (5H, m).

EXAMPLE-23

6-(2-N,N-Dimethylaminoethyl)-2,4-difluorobenzo[d]isothiazolo[3,2-a]indol-S,S-dioxide Using essentially the general procedure described in example 1 and some non-critical variations, the above derivative was prepared. Melting range (° C.): 180-182; IR spectra (cm$^{-1}$): 2963, 2789, 1593, 1347, 1184, 919, 796, 586; Mass (m/z): 363 (M+H)$^+$; $^1$H-NMR (δ ppm): 2.37 (6H, s), 2.54-2.63 (2H, s), 3.08-3.13 (2H, m), 6.93-7.90 (6H, m).

EXAMPLE-24

6-(2-N,N-dimethylaminoethyl)-4-fluoro-8-methyl-benzo[d]isothiazolo[3,2-a]indol-S,S-dioxide Using essentially the general procedure described in example 1 and some non-critical variations, the above derivative was prepared. Melting range (° C.): 158-160; Mass (m/z): 359 (M+H)$^+$; $^1$H-NMR (δ ppm): 2.41 (6H, s), 2.51 (3H, s), 2.59-2.67 (2H, m), 3.05-3.16 (2H, m), 7.05-7.74 (7H, m).

EXAMPLE-25

2,4-Difluoro-6-(2-N,N-dimethylaminoethyl)-8-methylbenzo[d]isothiazolo[3,2-a]indol-S,S-dioxide Using essentially the general procedure described in example 1 and some non-critical variations, the above derivative was prepared. Melting range (° C.): 182-184; Mass (m/z): 377 (M+H)$^+$; $^1$H-NMR (δ ppm): 2.42 (6H, s), 2.53 (3H, s), 2.60-2.68 (2H, m), 3.09-3.17 (2H, m), 6.87-7.77 (5H, m).

EXAMPLE-26

6-(2-N,N-Dimethylaminoethyl)-2-methoxybenzo[d]isothiazolo[3,2-a]indol-S,S-dioxide Using essentially the general procedure described in example 1 and some non-critical variations, the above derivative was prepared. IR spectra (cm$^{-1}$): 2935, 2781, 1342, 1184;

Mass (m/z): 357 (M+H)$^+$; $^1$H-NMR (δ ppm): 2.38 (6H, s), 2.56-2.64 (2H, m), 3.09-3.17 (2H, m), 4.08 (3H, s), 6.84-7.86 (7H, m).

EXAMPLE-27

6-(2-N,N-Dimethylaminoethyl)-2,8-dimethoxybenzo[d]isothiazolo[3,2-a]indol-S,S-dioxide Using essentially the general procedure described in example 1 and some non-critical variations, the above derivative was prepared. Mass (m/z): 387 (M+H)$^+$; $^1$H-NMR (δ ppm): 2.47 (6H, s), 2.68-2.77 (2H, m), 3.15-3.23 (2H, m), 3.94 (3H, s), 6.80-7.76 (7H, m).

EXAMPLE-28

6-(2-N,N-Dimethylaminoethyl)-8-methylbenzo[d]isothiazolo[3,2-a]indol-S,S-dioxide Using essentially the general procedure described in example 1 and some non-critical variations, the above derivative was prepared. Melting range (° C.): 156-158; Mass (m/z): 341 (M+H)$^+$; $^1$H-NMR (δ ppm): 2.40 (6H, s), 2.50 (3H, s), 2.58-2.66 (2H, m), 3.11-3.19 (2H, m), 7.22-7.74 (7H, m).

EXAMPLE-29

6-(3-N,N-Dimethylamino-1-hydroxyprop-1-yl)benzo[d]isothiazolo[3,2-a]indol-S,S-dioxide Using essentially the general procedure described in example 1 and some non-critical variations, the above derivative was prepared. Melting range (° C.): 144-146; IR spectra (cm$^{-1}$): 3307, 2826, 1602, 1331, 1182; Mass (m/z): 357 (M+H)$^+$.

EXAMPLE-30

4-Bromo-6-(3-N,N-Dimethylamino-1-hydroxyprop-1-yl)benzo[d]isothiazolo[3,2-a]indol-S,S-dioxide Using essentially the general procedure described in example 1 and making non-critical variations, the above derivative was prepared. IR spectra (cm$^-$): 3430, 2924, 2854, 1332; Mass (m/z): 435 (M+H)$^+$, 437 (M+H)$^+$.

EXAMPLE-31

6-(3-N,N-Dimethylamino-1-hydroxyprop-1-yl)-8-methoxybenzo[d]isothiazolo[3,2-a]indol-S,S-dioxide Using essentially the general procedure described in example 1 and making non-critical variations, the above derivative was prepared. IR spectra (cm$^{-1}$): 3405, 2927, 1587, 1447, 1365, 1174; Mass (m/z): 387 (M+H)$^+$.

EXAMPLE-32

6-(3-N,N-Dimethylamino-1-hydroxyprop-1-yl)-8-methylbenzo[d]isothiazolo[3,2-a]indol-S,S-dioxide Using essentially the general procedure described in example 1 and making non-critical variations, the above derivative was prepared. Melting range (° C.): 116-119; IR spectra (cm$^{-1}$): 3307, 3059, 2828, 1601, 1325, 1177; Mass (m/z): 371 (M+H)$^+$.

EXAMPLE-33

4-Bromo-6-(3-N,N-dimethylamino-1-hydroxyprop-1-yl)-8-methoxybenzo[d]isothiazolo[3,2-a]indol-S,S-dioxide Using essentially the general procedure described in example 37 and making non-critical variations, the above derivative was prepared. Melting range (° C.): 128-133; Mass (m/z): 465 (M+H)$^+$, 467 (M+H)$^+$.

EXAMPLE-34

6-[2-(4-Methylpiperazin-1-yl)ethyl]benzo[d]isothiazolo[3,2-a]indol-S,S-dioxide

Using essentially the general procedure described in example 1 and some non-critical variations, the above derivative was prepared. IR spectra (cm$^{-1}$): 2938, 2806, 1652, 1372, 1174; Mass (m/z): 382 (M+H)$^+$; $^1$H-NMR (δ ppm): 2.30 (3H, s), 2.53-3.0 (12H, m), 7.00-8.00 (8H, m).

EXAMPLE-35

6-[2-Morpholin-4-ylethyl]benzo[d]isothiazolo[3,2-a]indol-S,S-dioxide

Using essentially the general procedure described in example 1 and some non-critical variations, the above derivative was prepared. Melting range (° C.): 155-158; IR spectra (cm$^{-1}$): 2958, 1604, 1443, 1331, 1177; Mass (m/z): 369 (M+H)$^+$; $^1$H-NMR (δ ppm): 2.58-2.63 (4H, m), 2.68-2.73 (2H, m), 3.14-3.18 (2H, m), 3.75-3.79 (4H, m), 7.26-7.87 (8H, m).

EXAMPLE-36

6-(2-Pyrrolidin-1-ylethyl)benzo[d]isothiazolo[3,2-a]indol-S,S-dioxide

Using essentially the general procedure described in example 1 and some non-critical variations, the above derivative was prepared. IR spectra (cm$^{-1}$): 2951, 1604, 1444, 1323, 1180; Mass (m/z): 353 (M+H)$^+$; $^1$H-NMR (δ ppm): 1.85-1.87 (4H, bs), 2.64-2.68 (4H, bs), 2.75-2.83 (2H, m), 3.17-3.26 (2H, m), 7.30-7.80 (8H, m).

EXAMPLE-37

6-(2-Piperidin-1-yl)ethyl]benzo[d]isothiazolo[3,2-a]indol-S,S-dioxide

Using essentially the general procedure described in example 1 and some non-critical variations, the above derivative was prepared. IR spectra (cm$^{-1}$): 2931, 1604, 1442, 1330, 1181; Mass (m/z): 367 (M+H)$^+$; $^1$H-NMR (δ ppm): 1.60-1.69 (10H, m), 2.57-2.67 (2H, m), 3.16-3.20 (2H, m), 7.20-7.80 (8H, m).

EXAMPLE-38

4-Bromo-6-[2-morpholin-4-ylethyl]benzo[d]isothiazolo[3,2-a]indol-S,S-dioxide

Using essentially the general procedure described in example 1 and some non-critical variations, the above derivative was prepared. Melting range (° C.): 220-224; IR spectra (cm⁻¹): 2929, 2794, 1438, 1338, 1184, 769, 590; Mass (m/z): 447 (M+H)⁺, 449 (M+3)⁺; ¹H-NMR (δ ppm): 2.57-2.62 (4H, m), 2.62-2.70 (2H, m), 3.08-3.16 (2H, m), 3.74-3.78 (4H, m), 7.45-7.87 (7H, m).

EXAMPLE-39

4-Bromo-6-(2-pyrrolidin-1-ylethyl)benzo[d]isothiazolo[3,2-a]indol-S,S-dioxide

Using essentially the general procedure described in example 1 and some non-critical variations, the above derivative was prepared. Melting range (° C.): 140-144; IR spectra (cm–1): 2957, 2792, 1346, 1175, 764, 579; Mass (m/z): 431 (M+H)⁺, 433 (M+3)⁺; ¹H-NMR (δ ppm): 1.85-1.89 (4H, bs), 2.69-2.73 (4H, bs), 2.77-2.79 (2H, m), 3.13-3.21 (2H, m), 7.44-7.88 (7H, m).

EXAMPLE-40

4-Bromo-6-[2-(4-methylpiperazin-1-yl)ethyl]benzo[d]isothiazolo[3,2-a]indol-S,S-dioxide Using essentially the general procedure described in example 1 and some non-critical variations, the above derivative was prepared. Melting range (° C.): 180-182; IR spectra (cm–1): 2962, 2784, 1457, 1333, 1175, 797, 590; Mass (m/z): 460 (M+H)⁺, 462 (M+3)⁺; ¹H-NMR (δ ppm): 2.32-2.38 (3H, s), 2.43-2.73 (10H, m), 3.07-3.18 (3H, m), 7.44-7.87 (7H, m).

EXAMPLE-41

6-(3-(Piperidin-1-yl)-1-hydroxyprop-1-yl)benzo[d]isothiazolo[3,2-a]indol-S,S-dioxide Using essentially the general procedure described in example 1 and some non-critical variations, the above derivative was prepared. IR spectra (cm–1): 3175, 2939, 1598, 1343, 1177; Mass (m/z):397 (M+H)⁺.

EXAMPLE-42

6-(3-(Piperidin-1-yl)-1-hydroxyprop-1-yl)-8-methoxybenzo[d]isothiazolo[3,2-a]indol-S,S-dioxide Using essentially the general procedure described in example 1 and some non-critical variations, the above derivative was prepared. Melting range (° C.): 177-180; Mass (m/z): 427 (M+H)⁺.

EXAMPLE-43

4-Bromo-6-(3piperidin-1-yl)-1-hydroxyprop-1-yl)benzo[d]isothiazolo[3,2-a]indol-S,S-dioxide Using essentially the general procedure described in example 1 and some non-critical variations, the above derivative was prepared. IR spectra (cm–1): 2932, 1593, 1338, 1181, 800, 728; Mass (m/z): 475 (M+H)⁺.

EXAMPLE-44

4-Bromo-6-(34piperidin-1-yl)-1-hydroxyprop-1-yl)-8-methoxybenzo[d]isothiazolo[3,2-a]indol-S,S-dioxide Using essentially the general procedure described in example 1 and some non-critical variations, the above derivative was prepared. Melting range (° C.): 192-196; IR spectra (cm–1): 2927, 1594, 1326, 1172, 798; Mass (m/z): 507 (M+H)⁺, 509 (M+H)⁺.

EXAMPLE-45

6-(3-(Pyrrolidin-1-yl)-1-hydroxyprop-1-yl)benzo[d]isothiazolo[3,2-a]indol-S,S-dioxide Using essentially the general procedure described in example 1 and some non-critical variations, the above derivative was prepared. Melting range (° C.) 128-130; IR spectra (cm): 3321, 2962, 1598, 1336, 1180; Mass (m/z): 383 (M+H)⁺.

EXAMPLE-46

6-(3-(Pyrrolidin-1-yl)-1-hydroxyprop-1-yl)-8-methoxybenzo[d]isothiazolo[3,2-a]indol-S,S-dioxide Using essentially the general procedure described in example 1 and some non-critical variations, the above derivative was prepared. IR spectra (cm⁻¹): 3306, 2965, 1602, 1374, 1177; Mass (m/z): 413 (M+H)⁺.

EXAMPLE-47

6-(2-(N,N-Diethylamino)-2-methylethyl)benzo[d]isothiazolo[3,2-a]indol-S,S-dioxide Mass (m/z): 369 (M+H)⁺.

EXAMPLE-48

6-(2N,N-Dimethylamino-1-hydroxy-1-yl)benzo[d]isothiazolo[3,2-a]indol-S,S-dioxide Using essentially the general procedure described in example 1 and some non-critical variations, the above derivative was prepared. Mass (m/z): 343 (M+H)⁺.

EXAMPLE-49

4-Bromo-6-(2-(N,N-Dimethylamino-1-hydroxy-1-yl)benzo[d]isothiazolo[3,2-a]indol-S,S-dioxide Using essentially the general procedure described in example 1 and some non-critical variations, the above derivative was prepared. Melting range (° C.): 148-152; (m/z): 421 (M+H)⁺, 423 (M+H)⁺.

EXAMPLE-50

6-(2-(N,N-Dimethylaminoethyl)-2,4-difluoro-8-Methoxybenzo[d]isothiazolo[3,2-a]indol-S,S-dioxide Using essentially the general procedure described in example 1 and some non-critical variations, the above derivative was prepared. Melting range (° C.): 140-142; IR spectra (cm⁻¹): 2937, 1602, 1332, 1177, 795, 587; Mass (m/z): 393 (M+H)⁺; ¹H-NMR (δ ppm): 2.43 (6H, s), 2.62-2.70 (2H, m), 3.09-3.17 (2H, m), 3.96 (3H, s), 6.87-7.80 (5H, m).

EXAMPLE-51

6-(2-(N,N-Dimethylamino-2-methylethyl)benzo[d]isothiazolo[3,2-a]indol-S,S-dioxide Using essentially the general procedure described in example 1 and some non-critical variations, the above derivative was prepared. Mass (m/z): 341 (M+H)$^+$.

EXAMPLE-52

6-(2-(N,N-Dimethylaminoethyl)-4-chloro-8-methyl-benzo[d]isothiazolo[3,2-a]indol-S,S-dioxide Using essentially the general procedure described in example 1 and some non-critical variations, the above derivative was prepared. Melting range (° C.): above 250, Mass (m/z): 375 (M+H)$^+$; $^1$H-NMR (δ ppm): 2.63 (3H, s), 2.90 (6H, s), 3.24 (2H, m), 3.61 (2H, m), 7.32-7.74 (6H, m).

EXAMPLE-53

8-(2-(N,N-Dimethylaminoethyl)benzo[d]isothiazolo[3,2-a]benzo(g)indol-S,S-dioxide Using essentially the general procedure described in example 1 and some non-critical variations, the above derivative was prepared. Mass (m/z): 377 (M+H)$^+$;

We claim:
1. A compound formula (I), and its tautomeric forms, its stereoisomers, and its pharmaceutically acceptable salts,
wherein $R_1$, $R_2$, $R_3$, $R_4$, $R_5$, $R_6$, $R_7$, $R_8$, $R_9$, $R_{10}$, $R_{11}$ and $R_{12}$ may be same or different and each independently represent hydrogen, halogen, perhaloalkyl, hydroxy, amino, nitro, cyano, formyl, amidino, guanidino, substituted or unsubstituted groups selected from the group consisting of linear or branched ($C_1$-$C_{12}$)alkyl, ($C_2$-$C_{12}$)alkenyl, ($C_2$-$C_{12}$)alkynyl, ($C_3$-$C_7$)cycloalkyl, ($C_3$-$C_7$)cycloalkenyl, bicycloalkyl, bicycloalkenyl, ($C_1$-$C_{12}$)alkoxy, cyclo($C_3$-$C_7$)alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, and hydroxylamino; or the adjacent groups $R_1$ and $R_2$ or $R_2$ and $R_3$ or $R_3$ and $R_4$ or $R_5$ and $R_6$ or $R_6$ and $R_7$ or $R_7$ and $R_8$ together with carbon atoms to which they are attached may form a 5, 6, or 7 membered ring, which may further optionally contain one or more double bonds and/or one or more heteroatoms selected from the group consisting of the group "Oxygen", "Nitrogen", "Sulfur" and "Selenium"; or $R_9$ and $R_{10}$ or $R_{11}$ and $R_{12}$ together represent double bond attached to "Oxygen" or "Sulfur"; or $R_9$ and $R_{10}$ or $R_{11}$ and $R_{12}$ together with the carbon atoms to which they are attached may form a 3, 4, 5, or 6 membered ring, which may further optionally contain one or more double bonds, and/or one or more heteroatoms selected from the group consisting of the group "Oxygen", "Nitrogen", "Sulfur" and "Selenium,";

$R_{13}$ and $R_{14}$ may be same or different and each independently represents hydrogen, substituted or unsubstituted groups selected from the group consisting of linear or branched ($C_1$-$C_{12}$)alkyl, ($C_2$-$C_{12}$)alkenyl, ($C_2$-$C_{12}$)alkynyl, ($C_2$-$C_{12}$)alkanoyl ($C_3$-$C_7$)cycloalkyl, ($C_3$-$C_7$)cycloalkenyl, bicycloalkyl, bicycloalkenyl, aryl, aralkyl, heteroaryl, and heterocyclylalkyl; or $R_{13}$ and $R_{14}$ along with the nitrogen atom, may form a 3, 4, 5, 6 or 7-membered heterocyclic ring, wherein the ring may be further substituted, and it may have either one, two or three double bonds or "additional heteroatoms"; and "n" is an integer ranging from 1 to 8.

2. A compound according to claim 1, which is selected from the group consisting of:
    6-(2-N,N-Dimethylaminoethyl)benzo[d]isothiazolo[3,2-a]indol-S,S-dioxide;
    4-Bromo-6-(2-N,N-dimethylaminoethyl)benzo[d]isothiazolo[3,2-a]indol-S,S-dioxide;
    4-Chloro-6-(2-N,N-dimethylaminoethyl)-benzo[d]isothiazolo[3,2-a]indol-S,S-dioxide;
    6-(2-N,N-Dimethylaminoethyl)-4-fluorobenzo[d]isothiazolo[3,2-a]indol-S,S-dioxide;
    6-(2-N,N-Dimethylaminoethyl)-4-methylbenzo[d]isothiazolo[3,2-a]indol-S,S-dioxide;
    6-(2-N,N-Dimethylaminoethyl)-4-methylbenzo[d]isothiazolo[3,2-a]indol-S,S-dioxide hydrochloride salt;
    6-(2-N,N-Dimethylaminoethyl)-4-methylbenzo[d]isothiazolo[3,2-a]indol-S,S-dioxide maleate salt;
    6-(2-N,N-Dimethylaminoethyl)-4-methylbenzo[d]isothiazolo[3,2-a]indol-S,S-dioxide D,L-malic acid salt;
    6-(2-N,N-Dimethylaminoethyl)-4-methylbenzo[d]isothiazolo[3,2-a]indol-S,S-dioxide oxalate salt;
    6-(2-N,N-Dimethylaminoethyl)-4-methylbenzo[d]isothiazolo[3,2-a]indol-S,S-dioxide citrate salt;
    6-(2-N,N-Dimethylaminoethyl)-(methoxybenzo[d]isothiazolo[3,2-a]indol-S,S-dioxide;
    6-(2-N,N-Dimethylaminoethyl)-8-methoxybenzo[d]isothiazolo[3,2-a]indol-S,S-dioxide;
    4-Bromo-6-(2-N,N-dimethylaminoethyl)-8-methoxybenzo[d]isothiazolo[3,2-a]indol-S,S-dioxide;
    4-Chloro-6-(2-N,N-dimethylaminoethyl)-methoxybenzo[d]isothiazolo[3,2-a]indol-S,S-dioxide;
    6-(2-N,N-Dimethylaminoethyl)-4fluoro-8-methoxybenzo[d]isothiazolo[3,2-a]indol-S,S-dioxide;
    6-(2-N,N-Dimethylaminoethyl)-4methyl-8-methoxy-benzo[d]isothiazolo[3,2-a]indol-S,S-dioxide;
    6-(2-N,N-Dimethylaminoethyl)-4,8-dimethoxybenzo[d]isothiazolo[3,2-a]indol-S,S-dioxide;

6-(2-N,N-Dimethylaminoethyl)-2-ethylbenzo[d]isothiazolo[3,2-a]indol-S,S-dioxide;
2-Chloro-6-(2-N,N-dimethylaminoethyl)benzo[d]isothiazolo[3,2-a]indol-S,S-dioxide;
2,4-Dichloro-6-(2-N,N-dimethylaminoethyl)-benzo[d]isothiazolo[3,2-a]indol-S,S-dioxide;
2,3-Dichloro-6-(2-N,N-dimethylaminoethyl)-benzo[d]isothiazolo[3,2-a]indol-S,S-dioxide;
5-Chloro-6-(2-N,N-dimethylaminoethyl)-2-methylbenzo[d]isothiazolo[3,2-a]indol-S,S-dioxide;
2,4,5-Trichloro-6-(2-N,N-dimethylaminoethyl)-benzo[d]isothiazolo[3,2-a]indol-S,S-dioxide;
6-(2-N,N-Dimethylaminoethyl)-2,4-difluorobenzo[d]isothiazolo[3,2-a]indol-S,S-dioxide;
6-(2-N,N-dimethylaminoethyl)-4-fluoro-8-methylbenzo[d]isothiazolo[3,2-a]indol-S,S-dioxide;
2,4-Difluoro-6-(2-N,N-dimethylaminoethyl)-8-methyl-benzo[d]isothiazolo[3,2-a]indol-S,S-dioxide;
6-(2-N,N-Dimethylaminoethyl)-2-methoxybenzo[d]isothiazolo[3,2-a]indol-S,S-dioxide;
6-(2-N,N-Dimethylaminoethyl)-2,8-dimethoxybenzo[d]isothiazolo[3,2-a]indol-S,S-dioxide;
6-(2-N,N-Dimethylaminoethyl)-8-methylbenzo[d]isothiazolo[3,2-a]indol-S,S-dioxide;
6-(3-N,N-Dimethylamino-1-hydroxyprop-1-yl)benzo[d]isothiazolo[3,2-a]indol-S,S-dioxide;
4-Bromo-6-(3-N,N-Dimethylamino-1-hydroxyprop-1-yl)benzo[d]isothiazolo[3,2-a]indol-S,S-dioxide;
6-(3-N,N-Dimethylamino-1-hydroxyprop-1-yl)-8-methoxybenzo[d]isothiazolo[3,2-a]indol-S,S-dioxide;
6-(3-N,N-Dimethylamino-1-hydroxyprop-1-yl)-8-methylbenzo[d]isothiazolo[3,2-a]indol-S,S-dioxide;
4-Bromo-6-(3N,N-dimethylamino-1-hydroxyprop-1-yl)-8-methoxybenzo[d]isothiazolo(3,2-a]indol-S,S-dioxide;
6-[2-(4-Methylpiperazin-1-yl)ethyl]benzo[d]isothiazolo[3,2-a]indol-S,S-dioxide;
6-[2-Morpholin-4-ylethyl]benzo[d]isothiazolo[3,2-a]indol-S,S-dioxide;
6-(2-Pyrrolidin-1-ylethyl)benzo[d]isothiazolo[3,2-a]indol-S,S-dioxide;
6-(2-Piperidin-1-yl)ethyl]benzo[d]isothiazolo[3,2-a]indol-S,S-dioxide;
4-Bromo-6-[2-morpholin-4-ylethyl]benzo[d]isothiazolo[3,2-a]indol-S,S-dioxide;
4-Bromo-6-(2-pyrrolidin-1-ylethyl)benzo[d]isothiazolo[3,2-a]indol-S,S-dioxide;
4-Bromo-6-[2-(4-methylpiperazin-1-yl)ethyl]benzo[d]isothiazolo[3,2-a]indol-S,S-dioxide;
6-(3-(Piperidin-1-yl)-1-hydroxyprop-1-yl)benzo[d]isothiazolo[3,2-a]indol-S,S-dioxide;
6-(3-(Piperidin-1-yl)-1-hydroxyprop-1-yl)-8-methoxybenzo[d]isothiazolo[3,2-a]indol-S,S-dioxide;
4-Bromo-6-(3-(piperidin-1-yl)-1-hydroxyprop-1-yl)benzo[d]isothiazolo[3,2-a]indol-S,S-dioxide;
4-Bromo-6-(3-(piperidin-1-yl)-1-hydroxyprop-1-yl)-8-methoxybenzo[d]isothiazolo[3,2-a]indol-S,S-dioxide;
6-(3-(Pyrrolidin-1-yl)-1-hydroxyprop-1-yl)benzo[d]isothiazolo[3,2-a]indol-S,S-dioxide;
6-(3-(Pyrrolidin-1-yl)-1-hydroxyprop-1-yl)-8-methoxybenzo[d]isothiazolo[3,2-a]indol-S,S-dioxide;
6-(2-(N,N-Diethylamino)-2-methylethyl)benzo[d]isothiazolo[3,2-a]indol-S,S-dioxide;
6-(2-(N,N-Dimethylamino-1-hydroxy-1-yl)benzo[d]isothiazolo[3,2-a]indol-S,S-dioxide;
4-Bromo-6-(2-(N,N-Dimethylamino-1-hydroxy-1-yl)benzo[d]isothiazolo[3,2-a]indol-S,S-dioxide;
6-(2-(N,N-Dimethylaminoethyl)-2,4-difluoro-8-Methoxybenzo[d]isothiazolo[3,2-a]indol-S,S-dioxide;
6-(2-(N,N-Dimethylamino-2-methylethyl)benzo[d]isothiazolo[3,2-a]indol-S,S-dioxide;
4-Chloro-6-(2-(N,N-Dimethylaminoethyl)-8-methyl-benzo[d]isothiazolo[3,2-a]indol-S,S-dioxide;
8-(2-(N,N-Dimethylaminoethyl)benzo[d]isothiazolo[3,2-a]benzo(g)indol-S,S-dioxide, or its stereoisomers, its N-oxides, or its pharmaceutically acceptable salts.

3. A pharmaceutical composition comprising either of a pharmaceutically acceptable carrier, diluent/s, excipient/s or solvates along with a therapeutically effective amount of a compound according to claim 1, its tautomeric forms, its stereoisomers, its geometric forms, its N-oxides, or its pharmaceutically acceptable salts.

4. A pharmaceutical composition according to claim 3, in the form of a tablet, capsule, powder, lozenges, suppositories, syrup, solution, suspension or injectable, administered as a single dose or multiple dose units.

5. Intermediates of formula (III) are represented as given below,

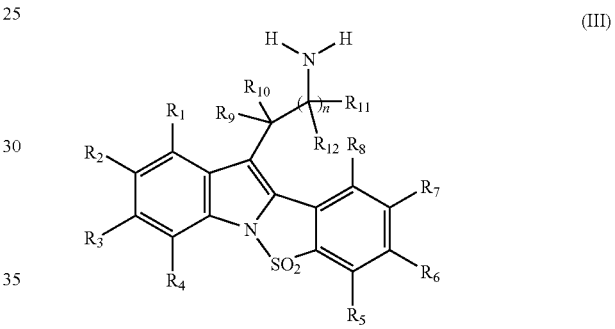

wherein $R_1, R_2, R_3, R_4, R_5, R_6, R_7, R_8, R_9, R_{10}, R_{11}$ and $R_{12}$ may be the same or different and each independently represent hydrogen, halogen, perhalalkyl, hydroxy, amino, nitro, cyano, formyl, amidino, guanidino, substituted or unsubstituted groups selected from the group consisting linear or branched $(C_1-C_{12})$alkyl, $(C_2-C_{12})$ alkenyl, $(C_2-C_{12})$alkynyl, $(C_3-C_7)$cycloalkyl, $(C_3-C_7)$ cycloalkenyl, bicycloalkyl, bicycloalkenyl, $(C_1-C_{12})$ alkoxy, cyclo$(C_3-C_7)$alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, and hydroxylamino, or the adjacent groups $R_1$ and $R_2$ or $R_2$ and $R_3$ or $R_3$ and $R_4$ or $R_5$ and $R_6$ or $R_6$ and $R_7$ or $R_7$ and $R_8$ together with carbon atoms to which they are attached may form a 5, 6, or 7 membered ring, which may further optionally contain one or more double bonds and/or one or more heteroatoms selected from the group consisting of the group "Oxygen", "Nitrogen", "Sulfur" or "Selenium" and combinations of double bond and heteroatoms; or $R_9$ and $R_{10}$ or $R_{11}$ and $R_{12}$ together represent double bond attached to "Oxygen" or "Sulfur"; or $R_9$ and $R_{10}$ or $R_{11}$ and $R_{12}$ together with the carbon atoms to which they are attached may form a 3, 4, 5, or 6 membered ring, which may further optionally contain one or more double bonds, and/or one or more heteroatoms selected from the group consisting of the group "Oxygen", "Nitrogen", "Sulfur" and "Selenium";

"n" is an integer ranging from 1 to 8.

6. The compound of claim 1, wherein n is 1 to 4.

7. The intermediates of claim 5, wherein n is 1 to 4.

* * * * *